United States Patent
Kamatani et al.

(10) Patent No.: US 8,952,367 B2
(45) Date of Patent: Feb. 10, 2015

(54) THIOXANTHONE COMPOUND AND ORGANIC LIGHT EMITTING ELEMENT HAVING THE SAME

(75) Inventors: Jun Kamatani, Tokyo (JP); Masanori Seki, Yokohama (JP); Takeshi Sekiguchi, Tokyo (JP); Yosuke Nishide, Kawasaki (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/881,586

(22) PCT Filed: Oct. 31, 2011

(86) PCT No.: PCT/JP2011/075526
§ 371 (c)(1),
(2), (4) Date: Apr. 25, 2013

(87) PCT Pub. No.: WO2012/063751
PCT Pub. Date: May 18, 2012

(65) Prior Publication Data
US 2013/0221340 A1    Aug. 29, 2013

(30) Foreign Application Priority Data

Nov. 8, 2010   (JP) .................................. 2010-249278

(51) Int. Cl.
*H01L 51/00* (2006.01)
*H01L 51/40* (2006.01)
(Continued)

(52) U.S. Cl.
CPC .......... H01L 51/0074 (2013.01); C07D 335/16 (2013.01); C07D 409/04 (2013.01);
(Continued)

(58) Field of Classification Search
USPC ....................... 257/40, 98, E51.001, E51.019; 313/504; 430/204, 296, 281.1, 300; 522/8, 63, 65
See application file for complete search history.

(56) References Cited

U.S. PATENT DOCUMENTS

2006/0241259 A1* 10/2006 Tanabe et al. ................. 526/217
2007/0224535 A1*  9/2007 Hoshi et al. ................... 430/204
(Continued)

FOREIGN PATENT DOCUMENTS

| JP | 3-177486 A | 8/1991 |
|----|------------|--------|
| JP | 11-54279 A | 2/1999 |

(Continued)

OTHER PUBLICATIONS

Cho, S-D, et al., "Suzuki-Miyaura Coupling Reaction of Aryl Chlorides Using di(2,6-dimethylmorpholino) Phenylphosphine As Ligand", Tetrahedron, vol. 63, No. 6, pp. 1345-1352 (2007).

(Continued)

*Primary Examiner* — Dao H Nguyen
(74) *Attorney, Agent, or Firm* — Fitzpatrick, Cella, Harper & Scinto

(57) ABSTRACT

Provided is an organic light emitting element having a high light emission efficiency and a low drive voltage. In the organic light emitting element including a positive electrode, a negative electrode and an organic compound layer disposed between the positive electrode and the negative electrode, the organic compound layer includes a thioxanthone compound represented by the following general formula [1].

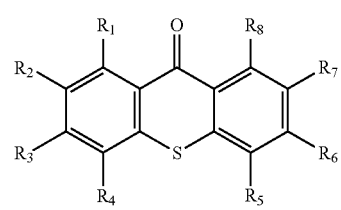

[1]

12 Claims, 1 Drawing Sheet

(51) Int. Cl.
*H01J 1/63* (2006.01)
*C08F 2/46* (2006.01)
*C07D 335/16* (2006.01)
*C07D 409/04* (2006.01)
*C07D 409/10* (2006.01)
*C07D 409/14* (2006.01)
*C09K 11/06* (2006.01)
*H05B 33/10* (2006.01)
*H01L 51/50* (2006.01)

(52) U.S. Cl.
CPC ............ *C07D409/10* (2013.01); *C07D 409/14* (2013.01); *H01L 51/0058* (2013.01); *H01L 51/0071* (2013.01); *C09K 11/06* (2013.01); *H05B 33/10* (2013.01); *H01L 51/5016* (2013.01); *H01L 51/5072* (2013.01); *H01L 51/5096* (2013.01); *C09K 2211/1007* (2013.01); *C09K 2211/1011* (2013.01); *C09K 2211/1088* (2013.01); *C09K 2211/1092* (2013.01)
USPC 257/40; 257/98; 257/E51.001; 257/E51.019; 313/504; 430/204; 430/296; 430/281.1; 430/300; 522/8; 522/63; 522/65

(56) References Cited

U.S. PATENT DOCUMENTS

2009/0066226 A1* 3/2009 Sugita et al. .................. 313/504
2011/0218266 A1* 9/2011 Studer et al. .................. 522/8

FOREIGN PATENT DOCUMENTS

| JP | 11-87057 A | 3/1999 |
| JP | 2001-126874 A | 5/2001 |
| JP | 2007-223955 A | 9/2007 |
| WO | 2006/114966 | 11/2006 |
| WO | 2011/136156 A1 | 11/2011 |
| WO | 2012/060234 A1 | 5/2012 |

OTHER PUBLICATIONS

Schoevaars, A.M., et al., "Toward a Switchable Molecular Rotor. Unexpected Dynamic Behavior of Functionalized Overcrowded Alkenes", J. Org. Chem., vol. 62, No. 15, pp. 4943-4948 (1997).

Hori, M., et al., "10-Thia-anthracenes. Part 3. A Reexamination of the Reaction of 9-Phenylthioxanthylium Salt and Phenyl-lithium", J. Chem. Soc., Perkin Trans. vol. 1, pp. 187-194 (1987).

Zinad, D. S. et al., "Site-selective Suzuki-Miyaura Reactions of the Bis (triflate) of 1, 3-dihydroxythioxanthone", Tetrahedron Letters, vol. 52, No. 27, pp. 3451-3454 (2011).

Chinese Office Action issued in counterpart application No. 201180053017.8 dated Dec. 4, 2013, along with its English-language translation—13 pages.

European Communication issued in counterpart application No. 11840271.8 dated Mar. 6, 2014—4 pages.

* cited by examiner

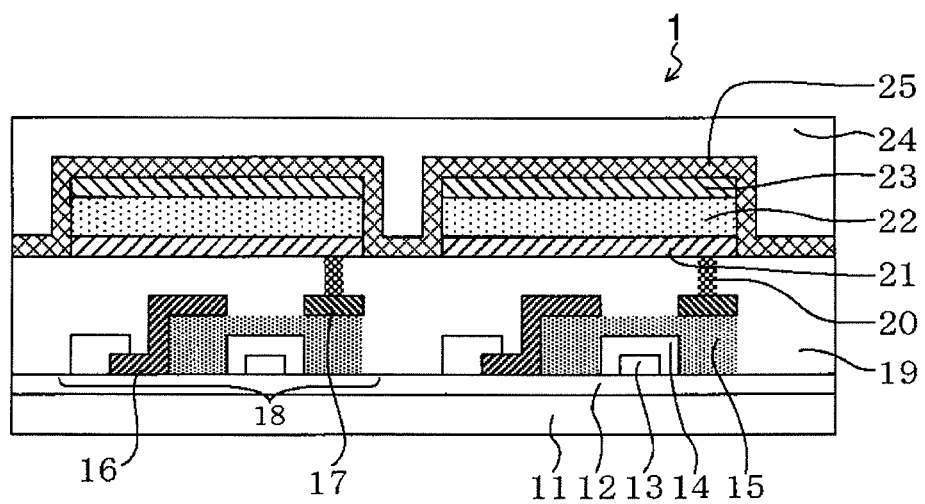

THIOXANTHONE COMPOUND AND ORGANIC LIGHT EMITTING ELEMENT HAVING THE SAME

TECHNICAL FIELD

The present invention relates to a thioxanthone compound and an organic light emitting element having the same.

BACKGROUND ART

An organic light emitting element is an electronic element having a positive (anode) electrode, a negative (cathode) electrode, and an organic compound layer disposed between both the electrodes. The organic light emitting element emits light when excitons generated by the recombination of holes and electrons injected from the respective electrodes in a light emitting layer contained in the organic compound layer return to the ground state. The recent organic light emitting device has remarkably advanced, and is characterized in that this organic light emitting device allows a thin and lightweight organic light emitting device which has low driving voltage, various emission wavelengths and rapid response to be produced.

Organic light emitting elements are broadly classified into fluorescent light emitting elements and phosphorescent light emitting elements according to the kind of excitons relevant to light emission. The phosphorescent light emitting element among them is an electronic element having a phosphorescent light emitting material in an organic compound layer constituting an organic light emitting element, specifically in a light emitting layer. The phosphorescent light emitting material absorbs energy generated by recombination of holes and electrons and generates triplet excitons. Thus, the phosphorescent light emitting element is an organic light emitting element capable of providing light emission originated from the triplet excitons.

Since the light emission quantum yield of phosphorescence can theoretically be made four times the quantum yield of fluorescence, attention has been focused on phosphorescent light emitting elements in recent years. However, there is room for further improvement in light emission efficiency in phosphorescent light emitting elements.

On the other hand, various proposals have been made on phosphorescent light emitting materials used in phosphorescent light emitting elements. As phosphorescent light emitting elements, for example, a compound H-1 (a thioxanthene compound, see Patent Literature 1) and a compound H-2 (a thioquinacridone compound, see Patent Literature 2) shown below are proposed.

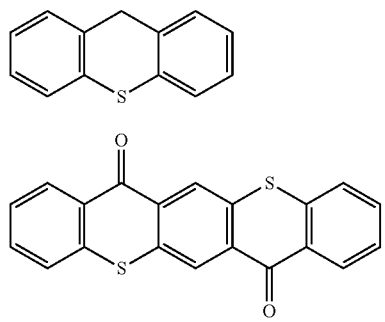

H-1

H-2

CITATION LIST

Patent Literature

PTL 1: Japanese Patent Application Laid-Open No. H03-177486
PTL 2: Japanese Patent Application Laid-Open No. H11-54279

The thioxanthene compound disclosed in Patent Literature 1, since having no ketone skeleton, has a shallow LUMO level. The thioquinacridone compound disclosed in Patent Literature 2, since having a fundamental skeleton of a narrow band gap, has a low $T_1$ energy.

On the other hand, in organic light emitting elements, in addition to light emitting materials contained in light emitting layers, electron transporting materials contained in electron transporting layers are required to be developed. Specifically, an organic compound which has a deep LUMO level of 2.7 eV or higher and is chemically stable is required.

Particularly in organic light emitting elements containing phosphorescent light emitting materials in the light emitting layers, light emitting materials and electron transporting materials which are materials constituting elements are required to have a high $T_1$ energy.

SUMMARY OF INVENTION

The present invention has been achieved in order to solve the above-mentioned problems, and has an object to provide an organic light emitting element having a high light emission efficiency and a low drive voltage.

The thioxanthone compound according to the present invention is represented by the following general formula [1].

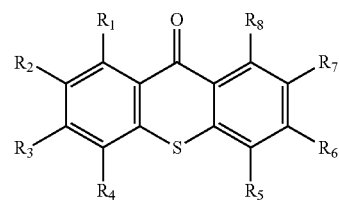

[1]

wherein $R_1$ to $R_8$ are each independently selected from a hydrogen atom, an alkyl group having 1 to 4 carbon atoms, or an aryl group selected from the group consisting of a phenyl group, a biphenyl group, a naphthyl group, a phenanthrene group, a fluorenyl group, a triphenylenyl group, a dibenzofuranyl group and a dibenzothiophenyl group; provided that at least one of $R_1$ to $R_8$ is the aryl group.

The alkyl group and the aryl group may further have an alkyl group, an aromatic hydrocarbon group or an aromatic heterocyclic group.

The thioxanthone compound according to the present invention is a compound having a high $T_1$ energy of 2.3 eV or more and a deep LUMO level of 2.7 eV or more. Thus, the present invention can provide an organic light emitting element having a high light emission efficiency and a low drive voltage.

BRIEF DESCRIPTION OF THE DRAWING

The single FIGURE is a sectional schematic diagram illustrating an organic light emitting element and a switching element connected to the organic light emitting element.

DESCRIPTION OF EMBODIMENTS

The thioxanthone compound according to the present invention is a compound represented by the following general formula [1].

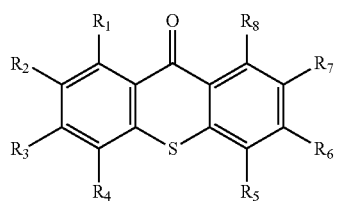

[1]

In the formula [1], $R_1$ to $R_8$ are each a hydrogen atom, an alkyl group having 1 to 4 carbon atoms, or an aryl group selected from the group consisting of a phenyl group, a biphenyl group, a naphthyl group, a phenanthrene group, a fluorenyl group, a triphenylenyl group, a dibenzofuranyl group and a dibenzothiophenyl group.

The alkyl group represented by $R_1$ to $R_8$ includes a methyl group, an ethyl group, an n-propyl group, an isopropyl group, an n-butyl group, an isobutyl group, a sec-butyl group and a tert-butyl group.

Provided that at least one of $R_1$ to $R_8$ is the aryl group.

The alkyl group and the aryl group may further have an alkyl group, an aromatic hydrocarbon group or an aromatic heterocyclic group.

The alkyl group which the alkyl group and the aryl group may further have includes, for example, a methyl group, an ethyl group, an n-propyl group, an isopropyl group, an n-butyl group, an isobutyl group, a sec-butyl group and a tert-butyl group.

The aromatic hydrocarbon group which the alkyl group and the aryl group may further have includes a phenyl group, a naphthyl group, a phenanthryl group and a fluorenyl group.

The aromatic heterocyclic group which the alkyl group and the aryl group may further have includes heteroaromatic ring groups such as a thienyl group, a dibenzofuranyl group, a dibenzothiophenyl group, a pyrrolyl group and a pyridyl group.

The alkyl group and the aryl group may further have an alkoxy group such as a methoxy group and an ethoxy group, an aryloxy group such as a phenoxy group and a naphthoxy group, and a halogen atom such as fluorine, chlorine, bromine and iodine.

The thioxanthone (thioxanthen-9-one) compound according to the present invention has a high $T_1$ energy of 3.0 eV and a deep LUMO level of 2.7 eV or more as thioxanthone itself. This is considered to bring about a high efficiency and an improvement of the stability of an organic light emitting element.

Then, a method of synthesizing the thioxanthone compound according to the present invention will be described. The thioxanthone compound of the present invention is synthesized, for example, by a synthesis scheme shown below. In the following synthesis scheme, Ar represents a phenyl group, a naphthyl group, a phenanthrene group, a fluorenyl group, a triphenylenyl group, a dibenzofuranyl group or a dibenzothiophenyl group.

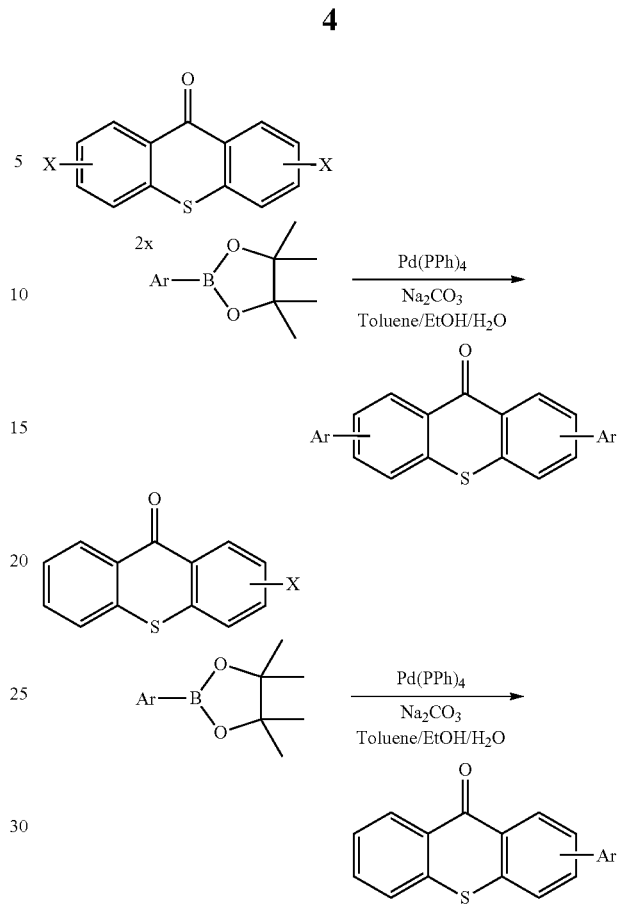

As shown in the above synthesis scheme, the thioxanthone compound according to the present invention can be synthesized by a coupling reaction of a halide (X) of thioxanthone with an arylboronic acid or an arylboronate ester by using a Pd catalyst. As the halide of thioxanthone, a commercially available one can be utilized.

Here in the case of synthesizing the thioxanthone compound according to the present invention by utilizing the above reaction scheme, a desired thioxanthone compound can be synthesized by suitably selecting Ar.

When the thioxanthone compound according to the present invention is used as a constituting material for an organic light emitting element, the thioxanthone compound is desirably refined by sublimation immediately before use. This is because the refinement by sublimation has a large refinement effect (high purification effect) from the viewpoint of high purification of an organic compound. However, when an organic compound is refined by sublimation, the compound having a higher molecular weight generally needs a higher temperature. Some compounds can easily undergo pyrolysis and the like because of high temperature. An organic compound used as a constituting material of an organic light emitting element desirably has a molecular weight of 1,000 or less so that the compound can be refined by sublimation under no excessive heating.

The thioxanthone compound according to the present invention, since the thioxanthone skeleton as the main skeleton has a carbonyl group, has a high electron affinity. Accordingly, the present inventors consider that the thioxanthone skeleton is a skeleton suitable for a compound to become an electron transporting material in consideration of the electron transporting capability originated from the carbonyl group.

The thioxanthone compound according to the present invention, since containing a carbon atom of a carbonyl group as a part of the cyclic structure in the thioxanthone skeleton, has a planar structure as a whole of the thioxanthone skeleton. The thioxanthone compound according to the present invention, since having this structure, easily causes the molecules to superpose to easily cause efficiently the intermolecular electron transfer in the solid state. From these structural properties, the thioxanthone compound according to the present invention can be said to be suitable as a constituting material for an organic light emitting element, specifically a material to bear a function of injecting and transporting electrons from a negative electrode or an adjacent layer. That is, the thioxanthone compound according to the present invention can be used suitably as an electron injecting and transporting material contained in an electron injecting and transporting layer, and a host of a light emitting layer.

Another feature which the thioxanthone skeleton exhibits includes a high $T_1$ energy. The $T_1$ energy can actually be determined from the 0-0 band acquired by a phosphorescent light spectrum measurement at 77K of a dilute toluene solution of non-substituted thioxanthone (a compound of the formula [1] in which $R_1$ to $R_8$ are each a hydrogen atom). As a result, the $T_1$ energy of non-substituted thioxanthone is 2.74 eV (451 nm), and is a sufficiently higher energy than that of a part of the blue region (455 nm to 480 nm) and the green region (490 nm to 530 nm). The thioxanthone compound according to the present invention can be applied essentially as an electron transporting material contained in an electron transporting layer, and a host of a light emitting layer in a phosphorescent light emitting element having a broad light emission color.

The compound H1 disclosed in Patent Literature 1 is a thioxanthene compound in which carbonyl of the thioxanthone skeleton is replaced with methylene. Here, although the compound H1 is excellent in the point of having a high $T_1$ energy (361 nm in terms of wavelength), since it has no carbonyl group present, the electron acceptance and the electron transportability as characteristics of thioxanthone compounds are largely decreased.

Here, the $T_1$ energies of main skeletons (thioxanthone skeleton, thioxanthene skeleton and thioquinacridone skeleton) of the thioxanthone compound according to the present invention and the compounds disclosed in Patent Literatures 1 and 2, respectively, were measured and calculated.

When the $T_1$ energies were determined by the measurements, the $T_1$ energies were determined from the measurement results of phosphorescent light spectra in the toluene solution state at 77K. More specifically, after phosphorescent light spectra were measured, the $T_1$ energies were determined from the 0-0 bands acquired in the measurements.

On the other hand, when the $T_1$ energies were determined by calculation, the molecular orbital calculations at the B3LYP/6-31G* level were carried out using the density functional theory. The values of the $T_1$ energies acquired by the calculations and measurements are shown in the following Table 1.

TABLE 1

| | Observed Value | Calculated Value | | |
|---|---|---|---|---|
| | $T_1$ [nm] | $T_1$ [nm] | HOMO [eV] | LUMO [eV] |
| Thioxanthone | 451 | 436 | −6.81 | −1.85 |
| Thioxanthene | 361 | 349 | −5.65 | −0.25 |
| Thioquinacridone | — | 549 | −5.80 | −2.53 |

From Table 1, it is indicated that LUMO of thioxanthene is shallower than that of thioxanthone. Thioquinacridone has a structure containing a thioxanthone skeleton, but thioquinacridone has a remarkably lower $T_1$ energy (about 570 nm in terms of wavelength) than the thioxanthone skeleton. Hence, thioquinacridone is a compound unsuitable as a constituting material for a phosphorescent light emitting element whose light emission color is blue or green.

From the above, in the compounds shown in Table 1, a compound having a $T_1$ energy suitable as a constituting material of a phosphorescent light emitting element whose light emission color is blue or green and having a deep HOMO suitable for the electron acceptance and the electron transportability is a thioxanthone compound only.

Meanwhile, the thioxanthene compound and the thioquinacridone compound disclosed in Patent Literatures 1 and 2 both have applications to fluorescent light emitting materials. By contrast, the thioxanthone compound according to the present invention is one used by paying attention to the electron transportability originated from the carbonyl group contained in the compound, and its application is an electron transporting material contained in an electron transporting layer and a host of a light emitting layer.

On the other hand, in the case where the thioxanthone compound according to the present invention is used as a compound other than a light emitting material for an electron transporting layer or a light emitting layer constituting an organic light emitting element, the following must be considered carefully. It is that the thioxanthone compound according to the present invention has an optimum band gap and a deeper LUMO in consideration of a light emission color of a light emitting material which the organic light emitting element has.

Here in the thioxanthone compound according to the present invention, in order to narrow the band gap of the compound, a substituent(s) having a conjugate such as an aryl group needs to be incorporated to a site(s) at which the thioxanthone skeleton and the conjugate are connected. The substitution position(s) becoming a site(s) at which the thioxanthone skeleton and the conjugate are connected is a 1- to 8-position carbon(s) of the thioxanthone skeleton shown below. Thus, an aryl group(s) is desirably incorporated to the 1- to 8-position(s) of the thioxanthone skeleton.

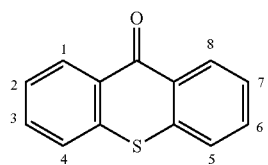 [SMILES: O=c1c2ccccc2sc2ccccc12]

In order to expand the conjugate which the compound has and control the band gap narrow, a substituent(s) is desirably placed at a substitution position(s) small in the steric hindrance against the thioxanthone skeleton. If taking this point into consideration, in the case of incorporating a substituent(s) to the thioxanthone skeleton, it is desirable that one or two positions to which substituents are incorporated are selected from $R_2$, $R_3$, $R_6$ and $R_7$ in the formula [1]. A combination of selection of one of $R_2$ and $R_3$ and selection of one of $R_6$ and $R_7$ is more desirable. A combination of $R_2$ and $R_7$ or a combination of $R_3$ and $R_6$ is especially desirable.

As for $R_1$, $R_4$, $R_5$ and $R_8$ in the formula [1], any thereof is desirably a hydrogen atom. In the case where a plurality of substituents is substituted, any of the substituents is desirably the same.

On the other hand, the incorporation of an alkyl group or an aromatic ring group to a skeleton having a high planarity as in the thioxanthone skeleton can improve the solubility to a solvent, the sublimability during vacuum deposition and the amorphousness in a thin film state. Here, when an alkyl group is incorporated, the incorporation of an alkyl group having 1 to 4 carbon atoms can improve the amorphousness without damaging the sublimability.

When the thioxanthone compound according to the present invention is used as an electron transporting material and a host of a light emitting layer being constituting materials of a phosphorescent light emitting element, the compound needs to have a higher $T_1$ energy than a phosphorescent light emitting material, and optimum HOMO-LUMO levels. Here, the incorporation of an aryl group to the thioxanthone skeleton can regulate the $T_1$ energy of the compound to some degree.

Particularly in an organic light emitting element having a phosphorescent light emitting material as a light emitting material, when the thioxanthone compound according to the present invention is used as a constituting material of a light emitting layer or a charge transporting layer (electron transporting layer) adjacent to the light emitting layer, the $T_1$ energy which the compound has becomes important. In the case where the light emission color of the phosphorescent light emitting material is blue to red, that is, has a maximum peak of the spectrum of the light emission wavelength of 455 nm or more and 620 nm or less, it is important to set the $T_1$ energy of the thioxanthone compound according to the present invention so as to correspond to the light emission color of the phosphorescent light emitting material.

In setting the $T_1$ energy of the thioxanthone compound according to the present invention, the present inventors paid attention to the $T_1$ energy of a substituent (condensed ring) incorporated to one of $R_1$ to $R_8$ in the formula [1]. The following Table 2 indicates the $T_1$ energies (values in terms of wavelength) of benzene and major condensed rings.

TABLE 2

| | $T_1$ (note 1) [nm] |
|---|---|
| Benzene | 339 |
| Naphthalene | 472 |
| Phenanthrene | 459 |
| Fluorene | 422 |
| Triphenylene | 427 |

TABLE 2-continued

| | $T_1$ [note 1] [nm] |
|---|---|
| Chrysene | 500 |
| Dibenzofuran | 417 |
| Dibenzothiophene | 415 |
| Anthracene | 672 |
| Pyrene | 589 |

[note 1] value in terms of wavelength

In consideration of Table 2, among benzene and condensed rings, benzene, naphthalene, phenanthrene, fluorene, triphenylene, chrysene, dibenzofuran, dibenzothiophene and pyrene can be said to be desirable.

Further in the case where the light emission color of a phosphorescent light emitting material is blue to green, a condensed ring desirable as a substituent (benzene and condensed rings) incorporated to the main skeleton of the thioxanthone compound according to the present invention is benzene, naphthalene, phenanthrene, fluorene, triphenylene, dibenzofuran or dibenzothiophene. Here, "blue to green" in this case refers to the range of 455 nm or more and 530 nm or less in wavelength, and does not include deep blue near 440 nm.

The substitution position of a substituent incorporated to the main skeleton of the thioxanthone compound according to the present invention, in order to more enhance the electron acceptability, is desirably a position to make LUMO of the compound itself deep. The following Table 3 indicates the substitution positions of a substituent (phenyl group) and relationships between HOMO energy and LUMO energy.

TABLE 3

| | HOMO[note 1] [eV] | LUMO[note 1] [eV] |
|---|---|---|
| 1-Position substitution | −6.11 | −1.83 |
| 2-Position substitution | −5.78 | −1.86 |
| 3-Position substitution | −5.92 | −1.92 |
| 4-Position substitution | −5.83 | −1.80 |

[note 1] Calculated value

From Table 3, even in the case where the same substituent (phenyl group) is substituted, the substitution of the substituent at $R_2$, $R_3$, $R_6$ or $R_7$ corresponding to the 2-position or 3-position substitution can be said to make LUMO of the thioxanthone compound deeper. Hence, when the thioxanthone compound according to the present invention is used as a material for an electron transporting layer and a light emitting layer requiring a height of electron acceptability, an aryl group(s) is desirably substituted at some of $R_2$, $R_3$, $R_6$ and $R_7$.

The compound according to the present invention can be used desirably for at least one of an electron transporting layer and a light emitting layer of an organic light emitting element emitting phosphorescent light. This is because the thioxanthone compound according to the present invention has a higher $T_1$ energy than that of a phosphorescent light emitting material. The thioxanthone compound according to the present invention has a suitably broad band gap even in the case of using the compound for such a layer, which is desirable.

Specific examples of the thioxanthone compound according to the present invention will be described hereinafter. However, the present invention is not limited thereto.
A-1
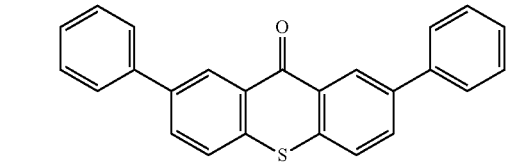
A-2
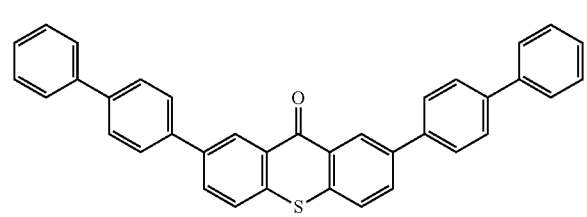
A-3
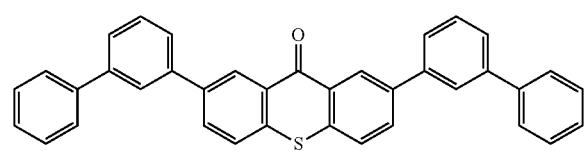
A-4
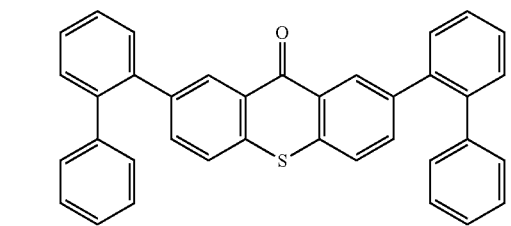
A-5
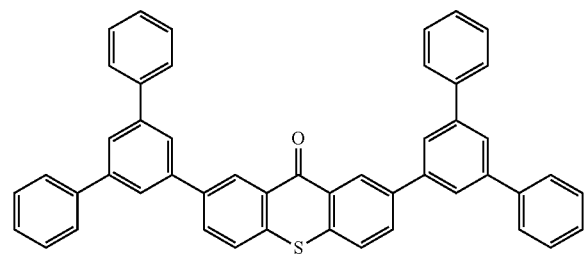
A-6
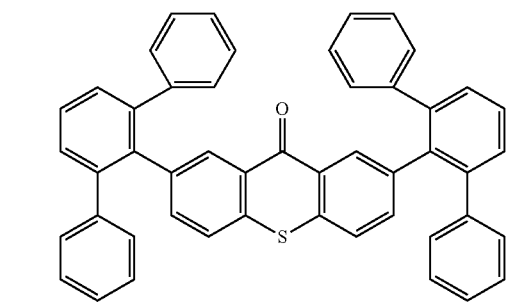
-continued
A-7
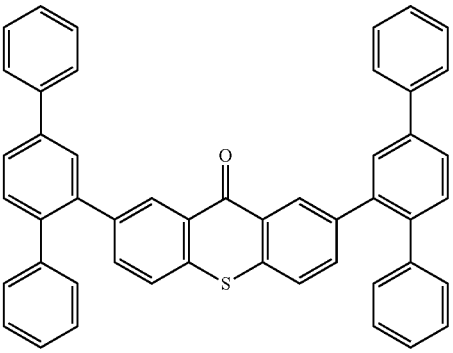
A-8
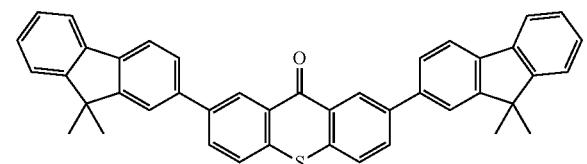
A-9
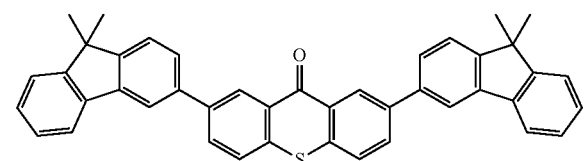
A-10
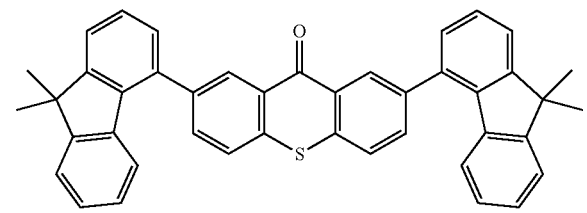
A-11
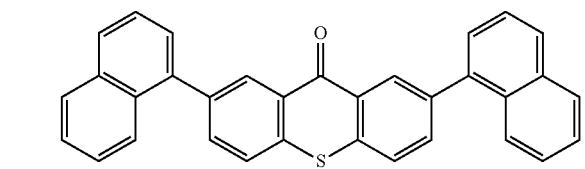
A-12
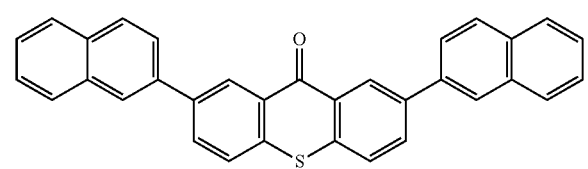
A-13

A-14
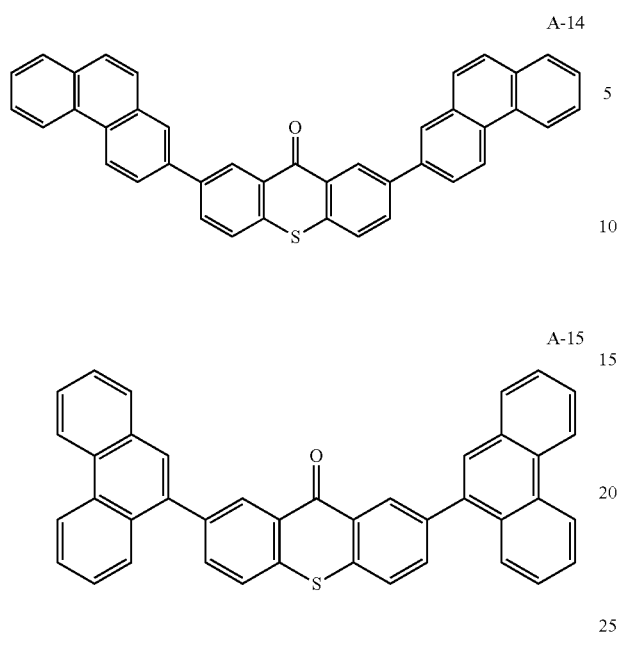
A-15
A-16
A-17
A-18
A-19
A-20
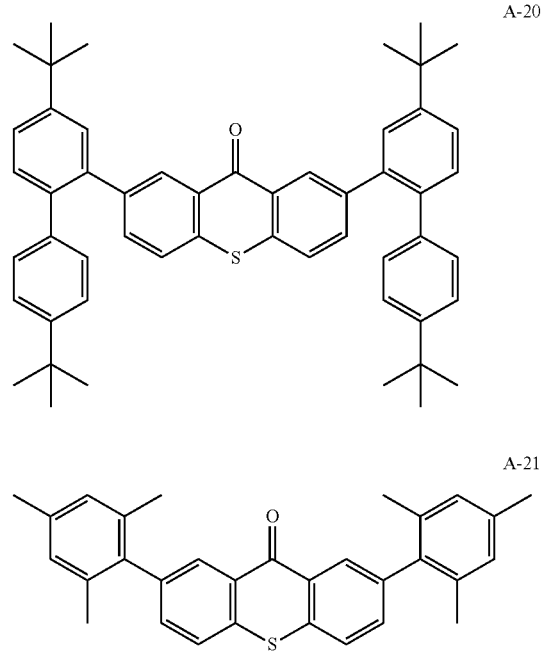
A-21
A-22
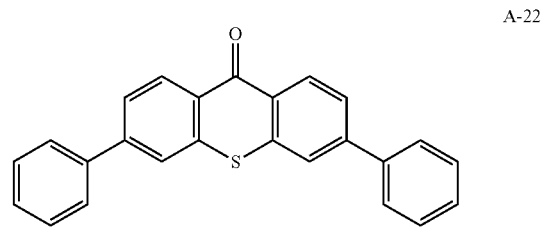
A-23
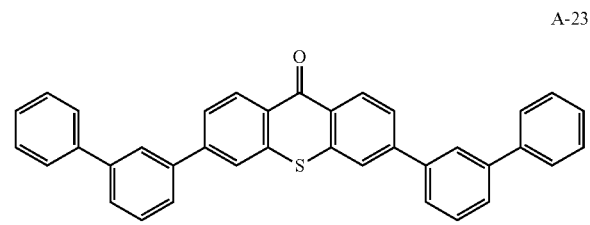
A-24
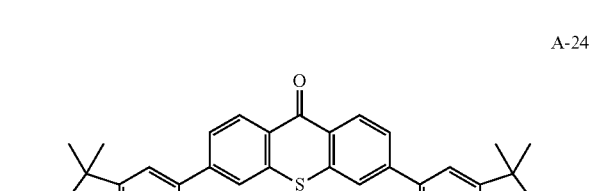
A-25
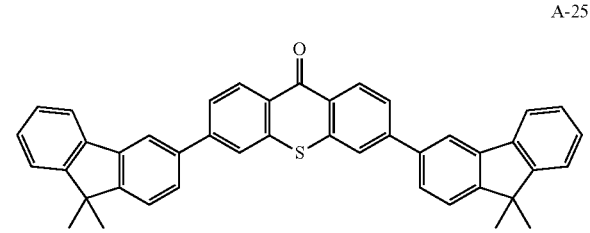

A-26
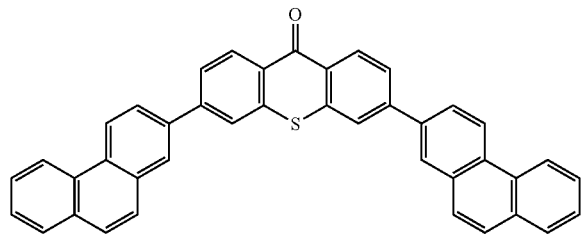
A-27
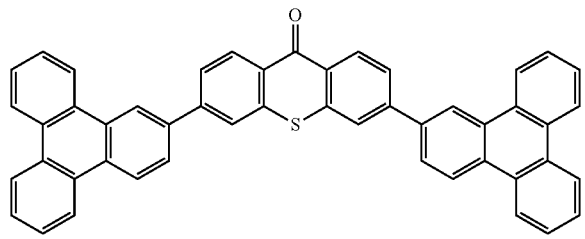
A-28
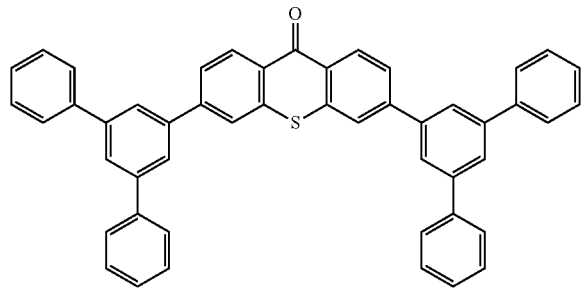
A-29
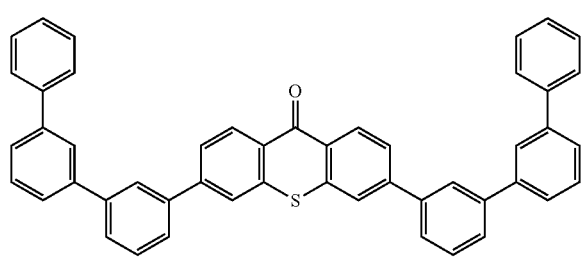
A-30
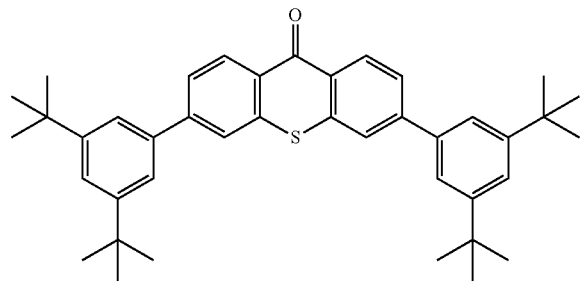
B-1
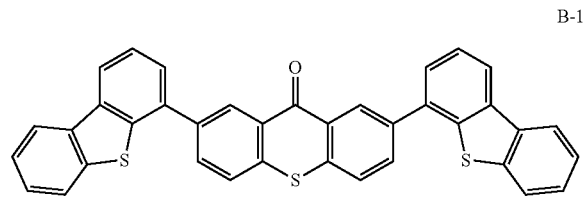
B-2
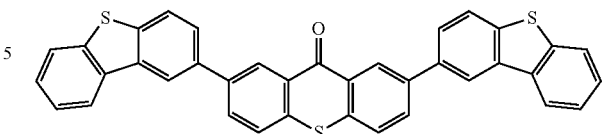
B-3
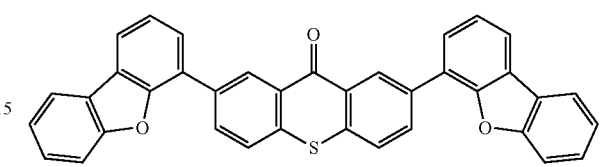
B-4
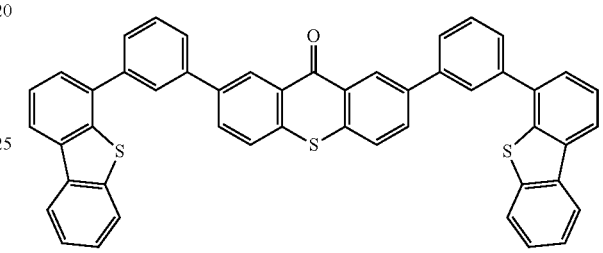
B-5
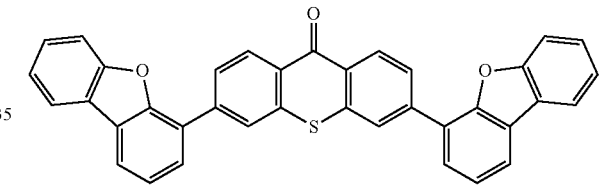
B-6
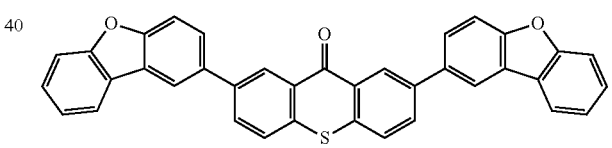
C-1
C-2
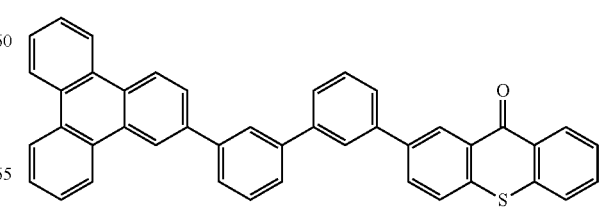

-continued
C-3
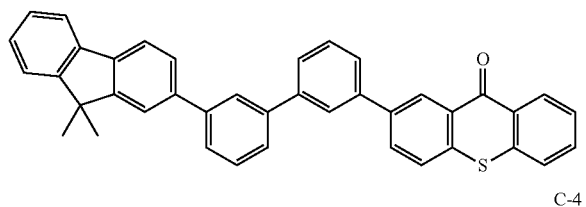
C-4
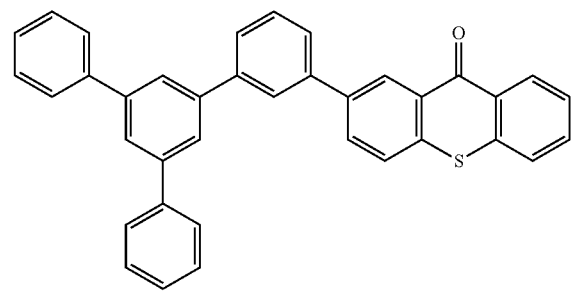
C-5
C-6
C-7
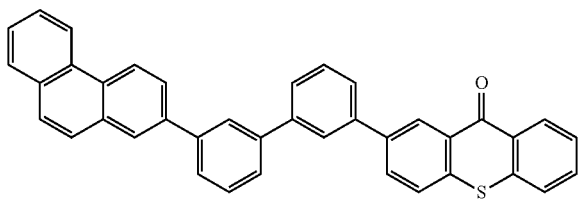
C-8
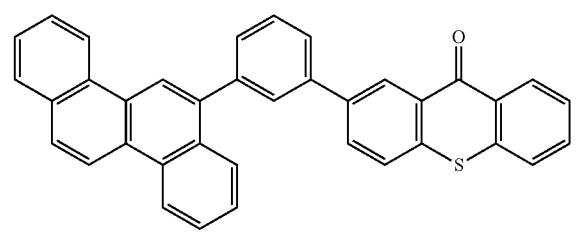
C-9
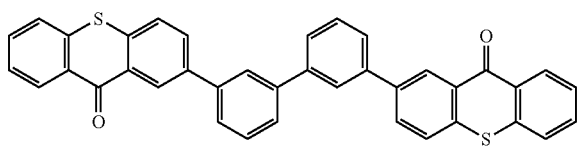
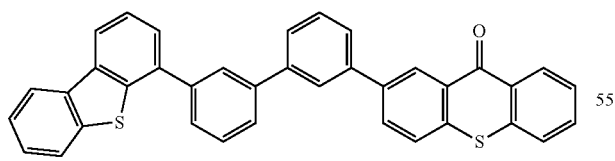
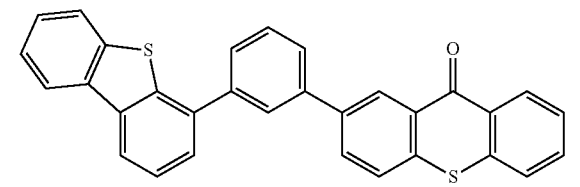
-continued
C-10
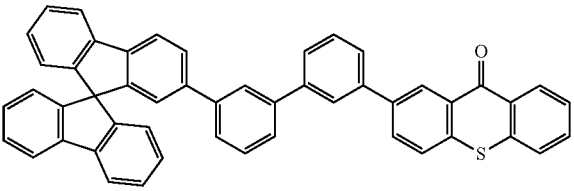
C-11
C-12
C-13
D-1
D-2
D-3
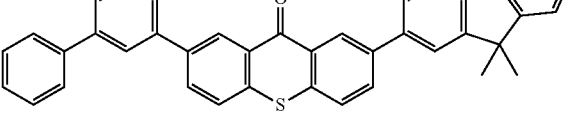

-continued

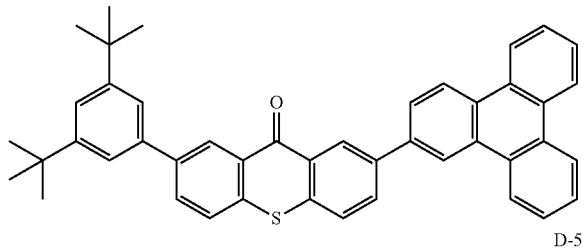

D-4

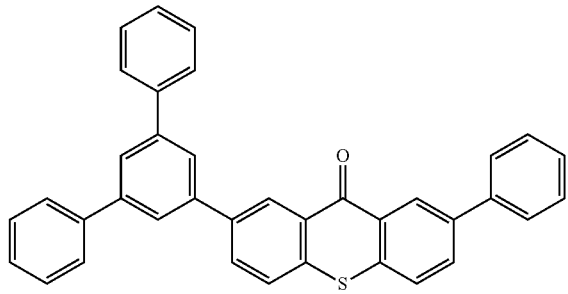

D-5

The compounds shown in the group A among the illustrative compounds are compounds in which the same substituents (alkyl group or aryl group) are incorporated at $R_2$ and $R_7$ or $R_3$ and $R_6$ in the thioxanthone skeleton represented by the formula [1]. The compounds shown in the group A have a stable skeleton having a symmetry axis by incorporation of two same substituents to predetermined positions of the thioxanthone skeleton as a central skeleton. Therefore, the compounds of the group A have a very high chemical stability and electron transportability as well. Therefore, if the compounds are used as an electron transporting material or a host or assist material contained in a light emitting layer, an elongated life of an element can be expected.

The compounds shown in the group B among the illustrative compounds are compounds in which heterocyclic groups or substituents containing a heterocycle are incorporated at some of $R_1$ to $R_8$ (for example, $R_2$ and $R_7$ or $R_3$ and $R_6$) in the thioxanthene skeleton represented by the formula [1]. The heterocyclic group having a hetero atom inside a cyclic group contained in the compounds shown in the group B, although not having so high a stability as aromatic hydrocarbon groups, has a stability near that of the aromatic hydrocarbon groups. Hence, if the compounds of the group B are used as an electron transporting material or a host or assist material contained in a light emitting layer, an elongated life of an element can be expected.

The compounds shown in the group C among the illustrative compounds are compounds in which a substituent (an alkyl group, an aryl group, a heterocyclic group or a complex substituent in combination thereof) is incorporated at one of $R_1$ to $R_8$ in the thioxanthene skeleton represented by the formula [1]. The compounds shown in the group C, since having no symmetry as a whole of the compound, have the CT property in HOMO-LUMO in some cases. Utilization of this can regulate the HOMO-LUMO to one suitable for a light emitting material. Hence, if the compounds of the group C are used as an electron transporting material or a host or an assist material contained in a light emitting layer, an elongated life of an element can be expected.

The compounds shown in the group D among the illustrative compounds are combinations of ideas of the group A to the group C, and by making the symmetry low, the solubility and the electron mobility of the compound itself can be controlled.

Then, the organic light emitting element according to the present invention will be described. The organic light emitting element according to the present invention includes a positive electrode and a negative electrode being a pair of electrodes opposing to each other, and an organic compound layer disposed between the positive electrode and the negative electrode. The organic compound layer contains the thioxanthone compound according to the present invention.

The organic compound layer constituting the organic light emitting element may be a single layer or a laminate composed of a plurality of layers as long as containing a light emitting layer or a layer having a light emission function. Here in the case where the organic compound layer is a laminate having a plurality of layers, the layers constituting the organic compound layer include a hole injecting layer, a hole transporting layer, a light emitting layer, a hole blocking layer, an electron transporting layer, an electron injecting layer and an exciton blocking layer. A plurality of layers from the layers described in the above group can be suitably selected, and combined and used.

However, the constitution of the organic light emitting element according to the present invention is not limited thereto. For example, a variety of layer structures can be employed including providing an insulating layer, an adhesive layer or an interfering layer at an interface between an electrode and an organic compound layer, and constituting an electron transporting layer or a hole transporting layer of two layers having different ionization potentials.

An element form of the organic light emitting element according to the present invention may be a so-called top emission system in which light is extracted from an electrode on the opposite side to a substrate, or a so-called bottom emission system in which light is extracted from an electrode on the substrate side. Alternatively, the structure may be such that a substrate and electrodes are made of light-transmissive materials, and light is extracted from both sides.

The thioxanthone compound according to the present invention is contained in an organic compound layer constituting an organic light emitting element, and is desirably contained in an electron transporting layer, a hole and exciton blocking layer, an electron injecting layer or a light emitting layer. Here in the case where the thioxanthone compound according to the present invention is contained in an electron transporting layer or a hole and exciton blocking layer, the thioxanthone compound according to the present invention is used as an electron transporting material.

Meanwhile, although a hole blocking layer is sometimes used as the meaning of a layer to block holes injected from a positive electrode (not permitting transfer of holes to the negative electrode direction), in the present invention, a layer adjacent to a light emitting layer on the negative electrode side of the light emitting layer is called a hole blocking layer. The reason therefor is that the thioxanthone compound according to the present invention is used originally not as a material to block holes, but as a material to transport electrons to a light emitting layer. However, because the position provided with the layer lies on the same position as for a usual hole blocking layer, and in order to avoid confusion with an electron transporting layer as for the arrangement position, the layer may be sometimes called a hole blocking layer by conforming to the arrangement position.

In the case where the thioxanthone compound according to the present invention is contained in a hole blocking layer, a light emitting layer may include a plurality of components, which can be classified into a major component and minor components. That is, these can be classified into a major component, which is a compound having a maximum weight ratio in all compounds constituting the light emitting layer, and minor components, which are components other than the major one.

Here, the major component is called a host. On the other hand, a minor component is called a guest (dopant), a light emission assist material or a charge injecting material depending on the functions of the materials themselves. The light emission assist material and the charge injecting material may be an organic compound having the same structure, or may be organic compounds having different structures. Although being a minor component, the minor component may also be called a second host in order to distinguish it from a guest and the like depending on the material of the component.

In the organic light emitting element according to the present invention, a guest refers to a compound mainly in charge of light emission in a light emitting layer. By contrast, a host refers to a compound present as a matrix around the guest in the light emitting layer, and a compound mainly in charge of transport of carriers and supply of excitation energy to the guest material. The host may have plural kinds of materials.

The concentration of a guest contained in a light emitting layer is 0.01% by weight or more and 50% by weight or less, and desirably 0.1% by weight or more and 20% by weight or less, based on the total amount of constituting materials of the light emitting layer. The concentration of the guest is more desirably 0.01% by weight or more and 10% by weight or less in order to prevent the concentration quenching. A guest may be contained homogeneously in the whole of a layer composed of a host, or may be contained with a concentration gradient. A guest may be partially contained in a specific region to partially provide a region of a host layer containing no guest.

The thioxanthone compound according to the present invention is used as a host of a light emitting layer corresponding to a phosphorescent light emitting material as a guest, a charge injecting material contained in the light emitting layer, or an electron transporting material contained in an electron transporting layer and a hole blocking layer. The light emission color of the phosphorescent light emitting material at this time is not especially limited, but the material is desirably a blue to green light emitting material with a maximum light emission peak wavelength in the range of 460 nm or more and 530 nm or less. The material is especially desirably a green light emitting material exhibiting a maximum light emission wavelength in the range of 490 nm or more and 530 nm or less.

In an organic light emitting element emitting phosphorescent light, in order to prevent a decrease in light emission efficiency due to nonradiative deactivation from $T_1$ of a host material, the host material is generally believed to need to have a higher $T_1$ energy than a phosphorescent light emitting material as a guest material.

The thioxanthone compound according to the present invention, since having a $T_1$ energy of 451 nm of the thioxanthone skeleton as a center of the compound, has a higher $T_1$ energy than a green phosphorescent light emitting material. Therefore, use of the compound for a light emitting layer or peripheral layers thereof of an organic light emitting element emitting green light can provide an organic light emitting element having a high light emission efficiency.

Further, the thioxanthone compound according to the present invention, since having a deep LUMO level, can be used not only as an electron injecting material, an electron transporting material or a constituting material of a hole blocking layer, but also as a second host contained in a light emitting layer. Use of the thioxanthone compound according to the present invention for applications indicated here can reduce a drive voltage of an element. This is because if the LUMO level is deep, the electron injection barrier from an electron transporting layer or a hole blocking layer adjacent to the negative electrode side of a light emitting layer is low.

On the other hand, in the case where the thioxanthone compound according to the present invention is contained in a light emitting layer, the light emitting layer may be a layer composed only of the thioxanthone compound according to the present invention, or may be a layer including a host and a guest. Here in the case where the light emitting layer includes a host and a guest, the thioxanthone compound according to the present invention is desirably used as a host.

Here in the case where the thioxanthone compound according to the present invention is used as a host of a light emitting layer, a corresponding guest is desirably a phosphorescent light emitting material. The phosphorescent light emitting material used as a guest is specifically a metal complex such as an iridium complex, a platinum complex, a rhenium complex, a copper complex, a europium complex and a ruthenium complex. Above all, an iridium complex exhibiting a strong phosphorescent light emissiveness is desirable. For the purpose of assisting the transfer of excitons and carriers, the light emitting layer may have a plurality of phosphorescent light emitting materials.

Specific examples of the iridium complex will be described hereinafter, but the present invention is not limited thereto.

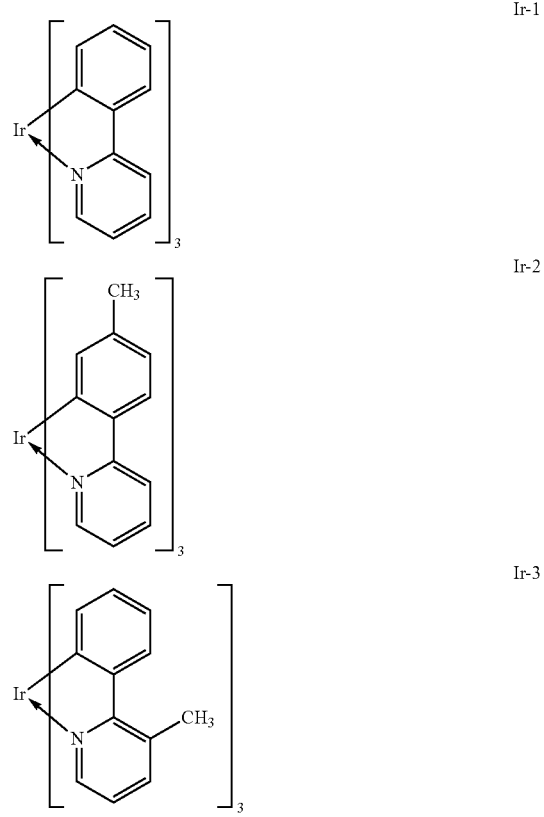

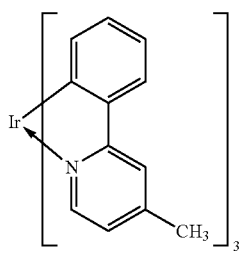
Ir-4
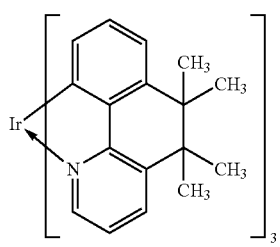
Ir-9
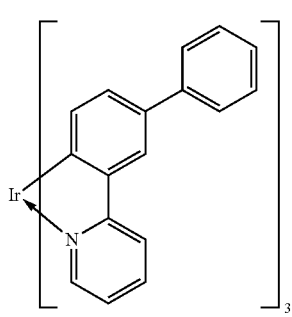
Ir-5
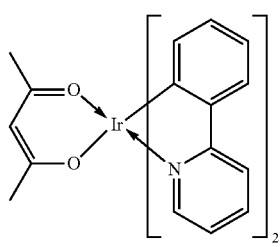
Ir-10
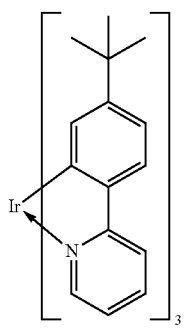
Ir-6
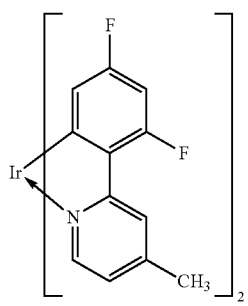
Ir-11
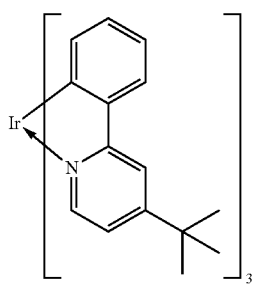
Ir-7
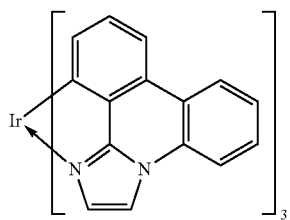
Ir-12
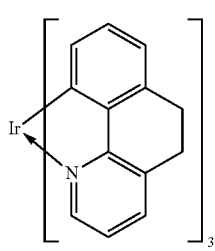
Ir-8
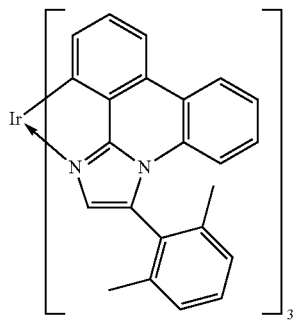
Ir-13

The host contained in a light emitting layer may be plural kinds thereof including the thioxanthone compound according to the present invention. Specific examples of a host (excluding the thioxanthone compound according to the present invention) used as a constituting material of the organic light emitting element according to the present invention will be described hereinafter, but the present invention is not limited thereto.

I-1

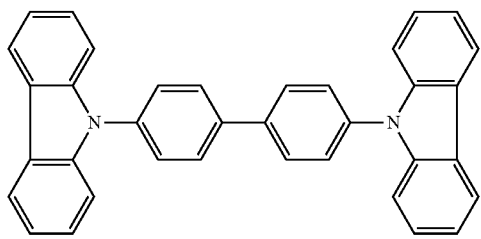

I-2

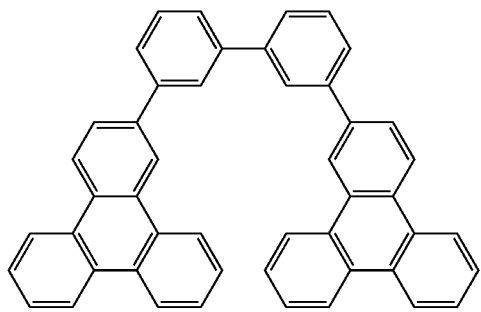

I-3

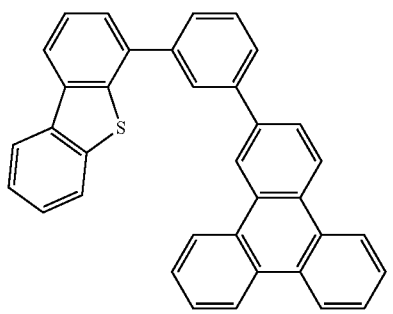

I-4

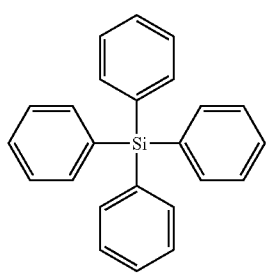

I-5

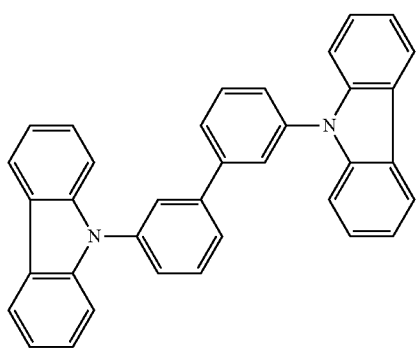

I-6

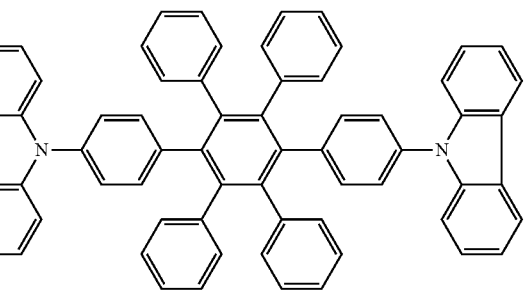

In the organic light emitting element according to the present invention, other than the thioxanthone compound according to the present invention, conventionally known low-molecular and high-molecular compounds can be used according to needs. More specifically, a hole injecting and transporting material, a host material, a light emitting compound, an electron injecting and transporting compound or the like can be used together. Examples of these compounds will be cited hereinafter.

As a hole injecting and transporting material, a material having a high hole mobility is desirable so that the injection of holes from a positive electrode is easy and the injected holes can be transported to a light emitting layer. Low-molecular and high-molecular materials having the hole injecting and transporting performance include triarylamine derivatives, phenylenediamine derivatives, stilbene derivatives, phthalocyanine derivatives, porphyrin derivatives, poly(vinylcarbazole), poly(thiophene) and other conductive polymers.

Light emitting materials mainly relevant to the light emission function include, other than the above-mentioned phosphorescent light emitting guest materials or derivatives thereof, polymer derivatives such as condensed ring compounds (for example, fluorene derivatives, naphthalene derivatives, pyrene derivatives, perylene derivatives, tetracene derivatives, anthracene derivatives and rubrene), quinacridone derivatives, coumarin derivatives, stilbene derivatives, organoaluminum complexes such as tris(8-quinolinolate)aluminum, organoberyllium complexes, and polymer derivatives such as poly(phenylene vinylene) derivatives, poly(fluorene) derivatives and poly(phenylene) derivatives.

An electron injecting and transporting material can be selected optionally from materials in which the injection of electrons from a negative electrode is easy and the injected electrons can be transported to the light emitting layer, and is selected in consideration of the balance with the hole mobility of the hole injecting and transporting material, and the like. Materials having the electron injecting and transporting performance include oxadiazole derivatives, oxazol derivatives, pyrazine derivatives, triazole derivatives, triazine derivatives, quinoline derivatives, quinoxaline derivatives, phenanthroline derivatives and organoaluminum complexes.

A material constituting a positive electrode is desirably one having as large a work function as possible. Examples usable are single metals such as gold, platinum, silver, copper, nickel, palladium, cobalt, selenium, vanadium and tungsten, or alloys in combination of two or more thereof, and metal oxides such as tin oxide, zinc oxide, indium oxide, indium tin oxide (ITO) and indium zinc oxide. Also usable are conductive polymers such as polyaniline, polypyrrole and polythiophene. These electrode substances may be used singly or may be used concurrently in two or more. A positive electrode may include one layer, or may include a plurality of layers.

On the other hand, a material constituting a negative electrode is desirably one having a small work function. Examples thereof include alkali metals such as lithium, alkaline earth metals such as calcium, and single metals such as aluminum, titanium, manganese, silver, lead and chromium. Also usable are alloys in combination of two or more of these single metals. Usable examples thereof are magnesium-silver, aluminum-lithium and aluminum-magnesium. Metal oxides such as indium tin oxide (ITO) can be utilized. These electrode substances may be used singly or may be used concurrently in two or more. A negative electrode may have a one-layer structure, or a multilayer structure.

In the organic light emitting element according to the present invention, a layer containing the organic compound according to the present invention, and a layer including another organic compound are formed by the following method. A thin film is formed generally by a vacuum deposition method, an ionization deposition method, a sputtering method, a plasma method, or a well-known coating method in which the compound is dissolved in a suitable solvent (for example, a spin coating method, a dipping method, a casting method, an LB method or an inkjet method). Here, if a layer is formed by a vacuum deposition method, a solution coating method or the like, the crystallization and the like hardly occur and the temporal stability is excellent. In the case where the film formation is carried out by a coating method, the film may be formed in combination of the compound with a suitable binder resin.

The binder resin includes polyvinylcarbazole resins, polycarbonate resins, polyester resins, ABS resins, acrylic resins, polyimide resins, phenol resins, epoxy resins, silicon resins and urea resins, but are not limited thereto. These binder resins may be used singly as a homopolymer or a copolymer, or may be used as a mixture of two or more. Further according to needs, well-known additives such as a plasticizer, an antioxidant and an ultraviolet absorbent may be used concurrently.

The organic light emitting element according to the present invention can be used for display apparatuses and illumination apparatuses. There are additionally exposure light sources of image forming apparatuses of the electrophotographic system, backlights of liquid crystal display apparatuses, and the like.

The display apparatus has the organic light emitting elements according to the present embodiment in a display section. The display section has a plurality of pixels. The pixel has the organic light emitting element according to the present embodiment and a TFT element as an example of a switching element to control the light emission intensity, and a positive electrode or a negative electrode of the organic light emitting element is connected with a drain electrode or a source electrode of the TFT element. The display apparatus can be used as an image display apparatus such as a PC.

The display apparatus has an input section to input image information from an area CCD, a linear CCD, a memory card and the like, or may be an image input apparatus to output an input image to a display section. The display apparatus may have both of an image output function to display image information input from the outside as a display section which an image pick-up apparatus or an inkjet printer has, and an input function to input processing information to an image as an operation panel. The display apparatus may be used as a display section of a multi-function printer.

Then, a display apparatus using the organic light emitting element according to the present embodiment will be described using the FIGURE.

The FIGURE is a sectional schematic diagram illustrating an example of a display apparatus using the organic light emitting element according to the present invention. In the display apparatus 1 in the FIGURE, two sets of a combination of the organic light emitting element and a TFT element are illustrated. The detail of the structure will be described hereinafter.

The display apparatus 1 in the FIGURE is provided with a substrate 1 composed of a glass or the like, and a moisture-proof film 2 to protect a TFT element or an organic compound layer over the substrate 1. There is illustrated a gate electrode 3 composed of a metallic material. There are further illustrated a gate insulating film 4 and a semiconductor layer 5.

The TFT element 8 has the semiconductor layer 5, a drain electrode 6, and a source electrode 7. An insulating film 9 is provided over the TFT element 8. Here in the display apparatus 1 in the FIGURE, a positive electrode 11 which an organic light emitting element has, and the source electrode 7 are connected through a contact hole 10. The display apparatus according to the present invention is not limited to the structure of the FIGURE, and suffices if either one of a positive electrode and a negative electrode are electrically connected with either one of a source electrode and a drain electrode which a TFT element has.

In the display apparatus in the FIGURE, an organic compound layer 22 is illustrated as a single layer. However, in the present invention, the organic compound layer 22 is not limited to a single layer, and may be a laminate composed of a plurality of layers. A first protecting layer 24 and a second protecting layer 25 to suppress the deterioration of the organic light emitting element are provided over the negative electrode 23.

Meanwhile, in the display apparatus 1 in the FIGURE, a switching element is not especially limited, and a single crystal silicon substrate or MIM element, an a-Si type element or the like may be used.

EXAMPLES

Example 1

Synthesis of Illustrative Compound A-1

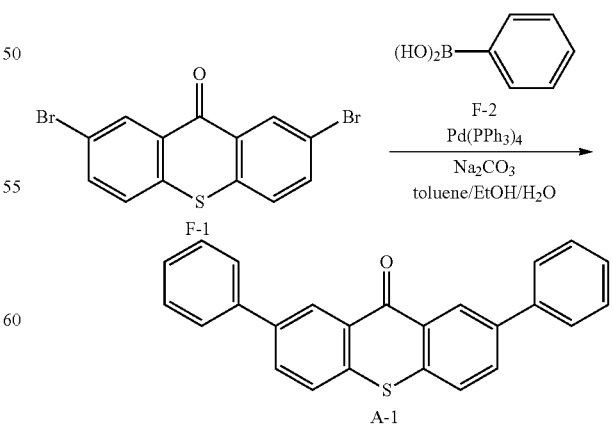

A 200-mL recovery flask was charged with the following reagents and solvents:

F-1: 1.85 g (5 mmol)
F-2 (phenylboronic acid): 1.5 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1\times10^{-4}$ Pa and 290° C. to obtain 1.45 g of high-purity illustrative compound A-1 (yield: 80%).

The obtained compound was identified by mass spectrometry.

[MALDI-TOF-MS (Matrix-Assisted Ionization-Time-of-Flight Mass Spectrometry)]

Observed value: m/z=364.55, calculated value: $C_{25}H_{16}OS$=364.09

Illustrative compound A-1 was measured for the $T_1$ energy by the following method. A prepared toluene dilute solution of illustrative compound A-1 was measured for a phosphorescent light spectrum at an excitation wavelength of 350 nm under an Ar atmosphere at 77K. The $T_1$ energy was determined from a peak wavelength of a first light emission peak of the obtained phosphorescent light spectrum. As a result, the $T_1$ energy was 475 nm in terms of wavelength.

Then, illustrative compound A-1 was measured for the energy gap by the following method. Illustrative compound A-1 was heat deposited on a glass substrate to obtain a deposited thin film of 20 nm in film thickness. The deposited thin film was measured for an absorbance spectrum by using an ultraviolet-visible spectrophotometer (V-560, made by JASCO Corp.). The energy gap of illustrative compound A-1 was determined from an absorption end of the obtained absorbance spectrum. As a result, the energy gap was 3.4 eV.

Example 2

Synthesis of Illustrative Compound A-3

-continued

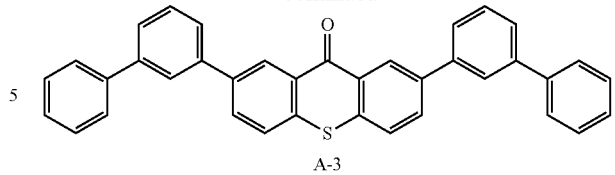

A-3

A 200-mL recovery flask was charged with the following reagents and solvents:

F-1: 1.85 g (5 mmol)
F-3 (3-biphenylboronic acid): 2.4 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1\times10^{-4}$ Pa and 310° C. to obtain 1.8 g of high-purity illustrative compound A-3 (yield: 70%).

[MALDI-TOF-MS]

Observed value: m/z=515.98, calculated value: 516.15
Illustrative compound A-3 was measured for the $T_1$ energy by the same method as in Example 1, and the $T_1$ energy was 474 nm in terms of wavelength. Illustrative compound A-3 was further measured for the energy gap by the same method as in Example 1, and the energy gap of illustrative compound A-3 was 3.3 eV.

Example 3

Synthesis of Illustrative Compound A-5

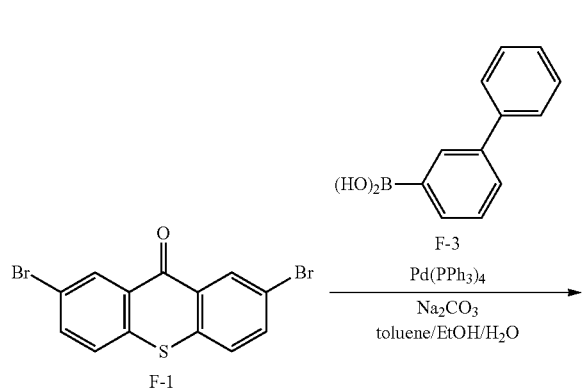

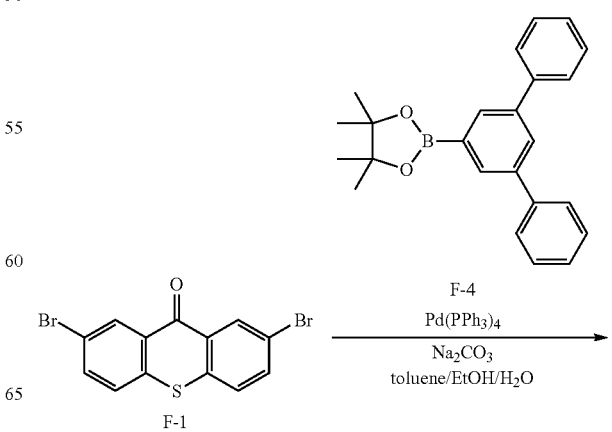

A-5

A 200-mL recovery flask was charged with the following reagents and solvents:

F-1: 1.85 g (5 mmol)
F-4: 4.3 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in chlorobenzene, and hot filtered, and thereafter, recrystallized twice with a chlorobenzene solvent to obtain a purified crystal. Then, the obtained crystal was vacuum dried at 100° C., and thereafter, refined by sublimation under the conditions of $1\times10^{-4}$ Pa and 380° C. to obtain 1.8 g of high-purity illustrative compound A-5 (yield: 55%).

[MALDI-TOF-MS]

Observed value: m/z=668.22, calculated value: 668.84

Illustrative compound A-5 was measured for the $T_1$ energy by the same method as in Example 1, and the $T_1$ energy was 475 nm in terms of wavelength. Illustrative compound A-5 was further measured for the energy gap by the same method as in Example 1, and the energy gap of illustrative compound A-5 was 3.3 eV.

Example 4

Synthesis of Illustrative Compound A-8

A-8

A 200-mL recovery flask was charged with the following reagents and solvents:

F-1: 1.85 g (5 mmol)
F-5: 2.9 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1\times10^{-4}$ Pa and 350° C. to obtain 2.2 g of high-purity illustrative compound A-8 (yield: 75%).

[MALDI-TOF-MS]

Observed value: m/z=596.45, calculated value: 596.22

Illustrative compound A-8 was measured for the $T_1$ energy by the same method as in Example 1, and the $T_1$ energy was 500 nm in terms of wavelength. Illustrative compound A-8 was further measured for the energy gap by the same method as in Example 1, and the energy gap of illustrative compound A-8 was 2.7 eV.

Example 5

Synthesis of Illustrative Compound A-9

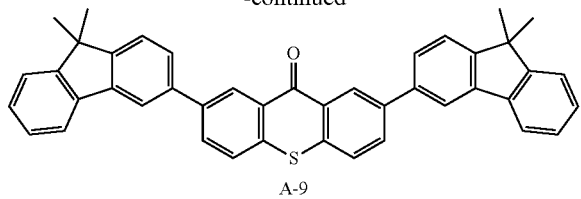

A-9

A 200-mL recovery flask was charged with the following reagents and solvents:
F-1: 1.85 g (5 mmol)
F-6: 2.9 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of 1×10⁻⁴ Pa and 340° C. to obtain 2.1 g of high-purity illustrative compound A-9 (yield: 71%).

[MALDI-TOF-MS]
Observed value: m/z=596.40, calculated value: 596.22
Illustrative compound A-9 was measured for the $T_1$ energy by the same method as in Example 1, and the $T_1$ energy was 482 nm in terms of wavelength.

Example 6

Synthesis of Illustrative Compound A-13

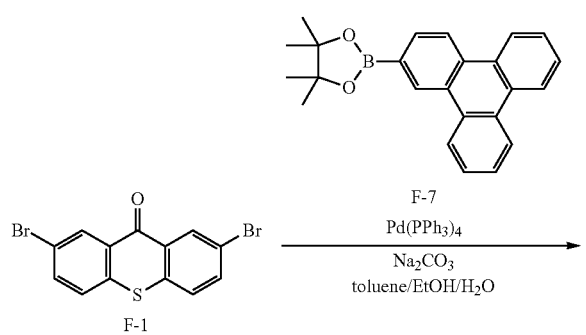

A 200-mL recovery flask was charged with the following reagents and solvents:
F-1: 1.85 g (5 mmol)
F-7: 4.3 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in chlorobenzene, and hot filtered, and thereafter, recrystallized twice with a chlorobenzene solvent to obtain a purified crystal. Then, the obtained crystal was vacuum dried at 120° C. to obtain 1.7 g of high-purity illustrative compound A-13 (yield: 50%).

[MALDI-TOF-MS]
Observed value: m/z=674.98, calculated value: 664.19
Illustrative compound A-13 was measured for the $T_1$ energy by the same method as in Example 1, and the $T_1$ energy was 503 nm in terms of wavelength.

Example 7

Synthesis of Illustrative Compound A-17

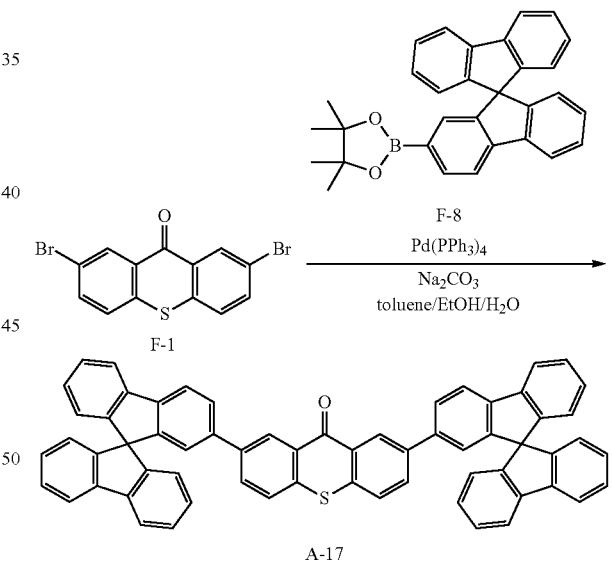

A 200-mL recovery flask was charged with the following reagents and solvents:
F-1: 1.85 g (5 mmol)
F-8: 5.3 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1\times10^{-4}$ Pa and 380° C. to obtain 3.0 g of high-purity illustrative compound A-17 (yield: 72%).

[MALDI-TOF-MS]

Observed value: m/z=840.77, calculated value: 840.25

Illustrative compound A-17 was measured for the $T_1$ energy by the same method as in Example 1, and the $T_1$ energy was 500 nm in terms of wavelength. Illustrative compound A-17 was further measured for the energy gap by the same method as in Example 1, and the energy gap of illustrative compound A-17 was 2.7 eV.

Example 8

Synthesis of Illustrative Compound A-21

A 200-mL recovery flask was charged with the following reagents and solvents:
F-1: 1.9 g (5 mmol)
F-9: 2.0 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1\times10^{-4}$ Pa and 310° C. to obtain 1.7 g of high-purity illustrative compound A-21 (yield: 74%).

[MALDI-TOF-MS]

Observed value: m/z=448.69, calculated value: 448.19

Illustrative compound A-21 was measured for the $T_1$ energy by the same method as in Example 1, and the $T_1$ energy was 463 nm in terms of wavelength.

Example 9

Synthesis of Illustrative Compound A-25

A 200-mL recovery flask was charged with the following reagents and solvents:
F-10: 1.85 g (5 mmol)
F-6: 2.9 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1\times10^{-4}$ Pa and 340° C. to obtain 1.9 g of high-purity illustrative compound A-25 (yield: 64%).

[MALDI-TOF-MS]

Observed value: m/z=596.89, calculated value: 596.22

Illustrative compound A-25 was measured for the $T_1$ energy by the same method as in Example 1, and the $T_1$ energy was 484 nm in terms of wavelength.

Example 10

Synthesis of Illustrative Compound B-1

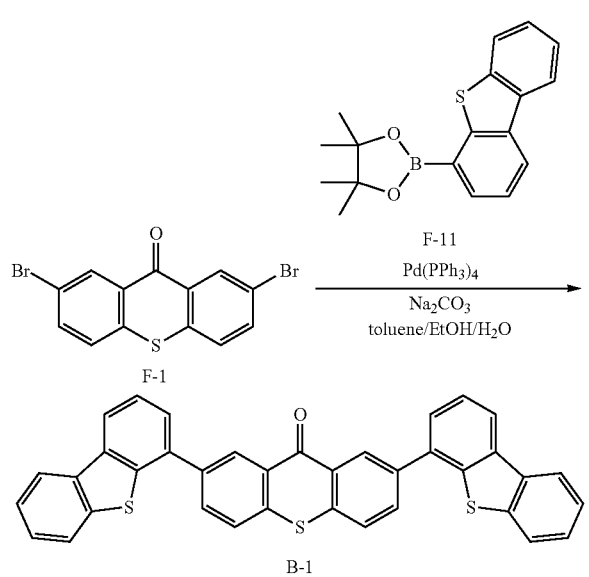

Example 11

Synthesis of Illustrative Compound B-2

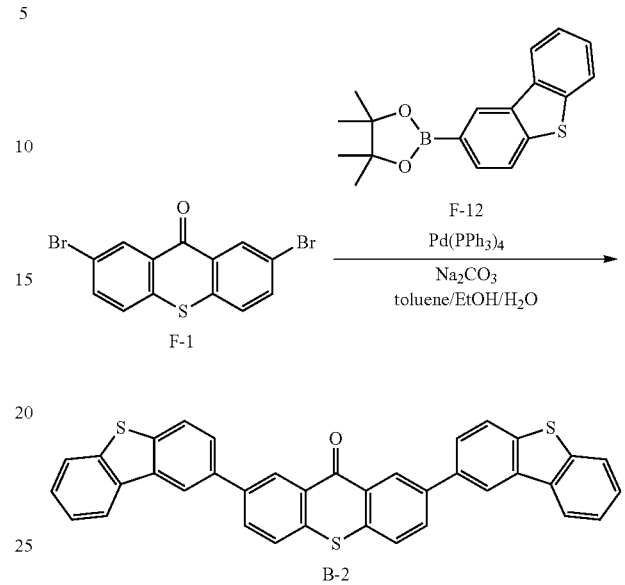

A 200-mL recovery flask was charged with the following reagents and solvents:

F-1: 1.85 g (5 mmol)

F-11: 3.7 g (12 mmol)

Tetrakis(triphenylphosphine)palladium(0): 137 mg (0.12 mmol)

Toluene: 50 mL

Ethanol: 20 mL

Sodium carbonate aqueous solution (concentration: 30% by weight): 30 mL

Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1 \times 10^{-4}$ Pa and 340° C. to obtain 1.7 g of high-purity illustrative compound B-1 (yield: 59%).

[MALDI-TOF-MS]

Observed value: m/z=576.67, calculated value: 576.07

Illustrative compound B-1 was measured for the $T_1$ energy by the same method as in Example 1, and the $T_1$ energy was 456 nm in terms of wavelength. Illustrative compound B-1 was further measured for the energy gap by the same method as in Example 1, and the energy gap of illustrative compound B-1 was 3.5 eV.

A 200-mL recovery flask was charged with the following reagents and solvents:

F-1: 1.85 g (5 mmol)

F-12: 3.7 g (12 mmol)

Tetrakis(triphenylphosphine)palladium(0): 137 mg (0.12 mmol)

Toluene: 50 mL

Ethanol: 20 mL

Sodium carbonate aqueous solution (concentration: 30% by weight): 30 mL

Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1 \times 10^{-4}$ Pa and 330° C. to obtain 1.9 g of high-purity illustrative compound B-2 (yield: 65%).

[MALDI-TOF-MS]

Observed value: m/z=576.46, calculated value: 576.07

Illustrative compound B-2 was measured for the $T_1$ energy by the same method as in Example 1, and the $T_1$ energy was 455 nm in terms of wavelength. Illustrative compound B-2 was further measured for the energy gap by the same method as in Example 1, and the energy gap of illustrative compound B-2 was 3.5 eV.

Example 12

Synthesis of Illustrative Compound B-3

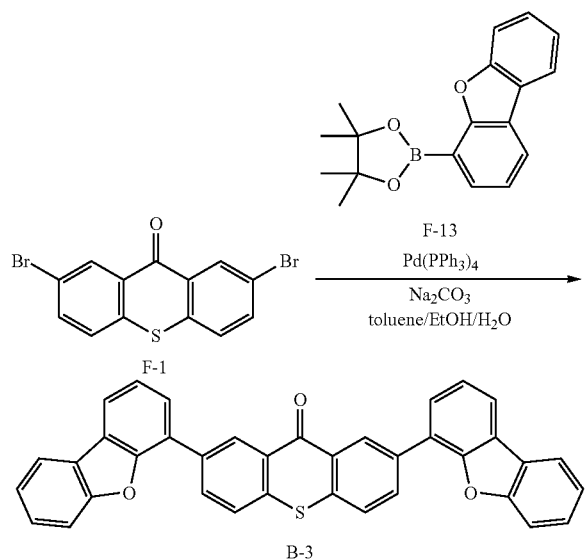

A 200-mL recovery flask was charged with the following reagents and solvents:
F-1: 1.85 g (5 mmol)
F-13: 3.5 g (12 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1\times10^{-4}$ Pa and 330° C. to obtain 1.5 g of high-purity illustrative compound B-3 (yield: 56%).

[MALDI-TOF-MS]
Observed value: m/z=544.87, calculated value: $C_{37}H_{20}O_3S$=544.11

Illustrative compound B-3 was measured for the $T_1$ energy by the same method as in Example 1, and the $T_1$ energy was 454 nm in terms of wavelength. Illustrative compound B-3 was further measured for the energy gap by the same method as in Example 1, and the energy gap of illustrative compound B-3 was 3.5 eV.

Example 13

Synthesis of Illustrative Compound C-2

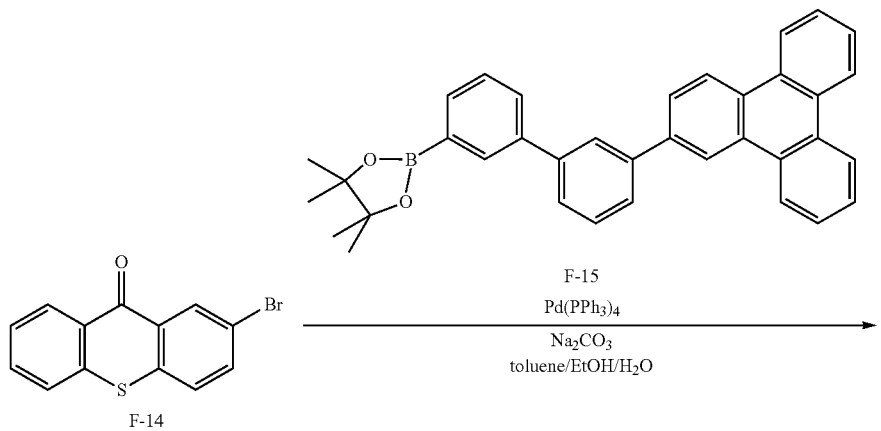

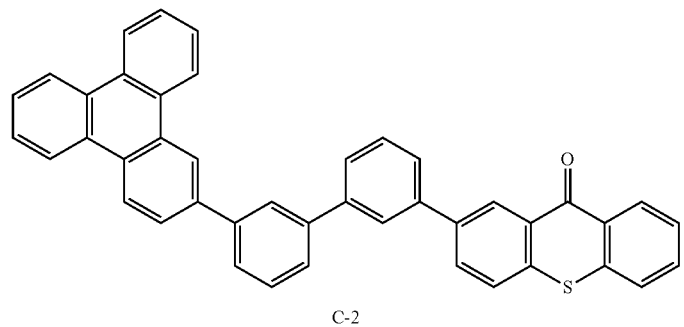

A 200-mL recovery flask was charged with the following reagents and solvents:

F-14: 1.45 g (5 mmol)
F-15: 3.0 g (6 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1\times10^{-4}$ Pa and 330° C. to obtain 2.2 g of high-purity illustrative compound C-2 (yield: 76%).

[MALDI-TOF-MS]

Observed value: m/z=590.84, calculated value: 590.17

Illustrative compound C-2 was measured for the $T_1$ energy by the same method as in Example 1, and the $T_1$ energy was 490 nm in terms of wavelength. Illustrative compound C-2 was further measured for the energy gap by the same method as in Example 1, and the energy gap of illustrative compound C-2 was 3.6 eV.

Example 14

Synthesis of Illustrative Compound C-7

A 200-mL recovery flask was charged with the following reagents and solvents:

F-14: 3.5 g (12 mmol)
F-16: 2.0 g (5 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1\times10^{-4}$ Pa and 330° C. to obtain 2.2 g of high-purity illustrative compound C-7 (yield: 77%).

[MALDI-TOF-MS]

Observed value: m/z=574.79, calculated value: 574.11

Illustrative compound C-7 was measured for the $T_1$ energy by the same method as in Example 1, and the $T_1$ energy was 470 nm in terms of wavelength. Illustrative compound C-7 was further measured for the energy gap by the same method as in Example 1, and the energy gap of illustrative compound C-7 was 3.4 eV.

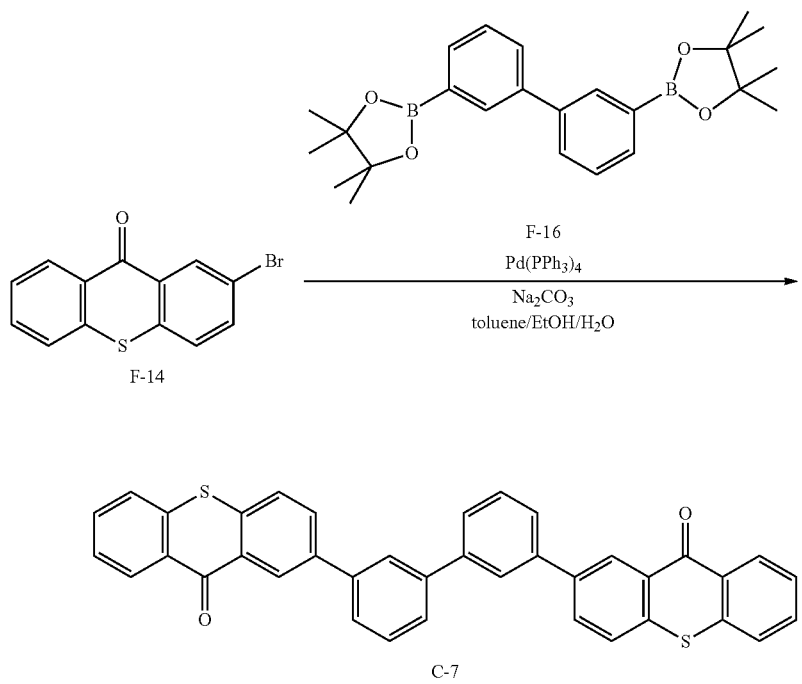

Example 15

Synthesis of Illustrative Compound C-9

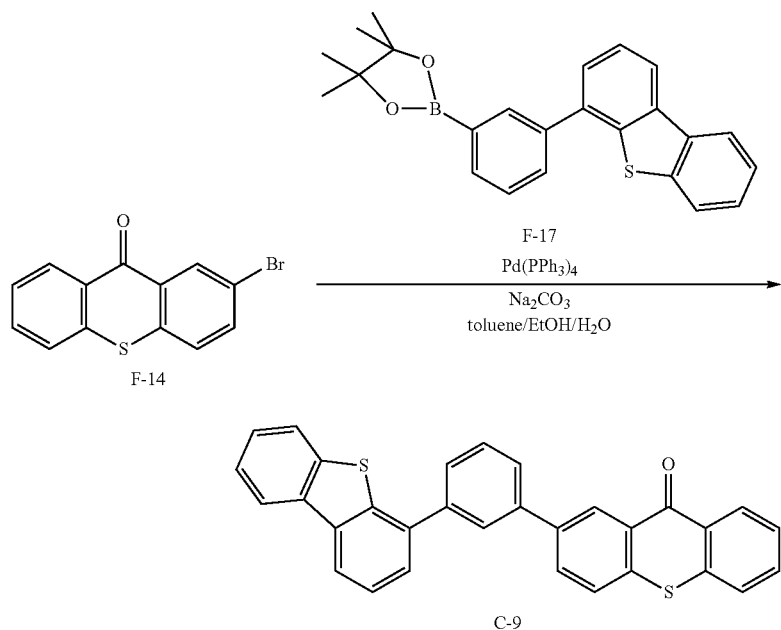

A 200-mL recovery flask was charged with the following reagents and solvents:
F-14: 1.45 g (5 mmol)
F-17: 2.3 g (6 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1 \times 10^{-4}$ Pa and 310° C. to obtain 1.5 g of high-purity illustrative compound C-9 (yield: 63%).

[MALDI-TOF-MS]

Observed value: m/z=470.54, calculated value: 470.08 Illustrative compound C-9 was measured for the $T_1$ energy by the same method as in Example 1, and the $T_1$ energy was 453 nm in terms of wavelength. Illustrative compound C-9 was further measured for the energy gap by the same method as in Example 1, and the energy gap of illustrative compound C-9 was 3.5 eV.

Example 16

Synthesis of Illustrative Compound C-10

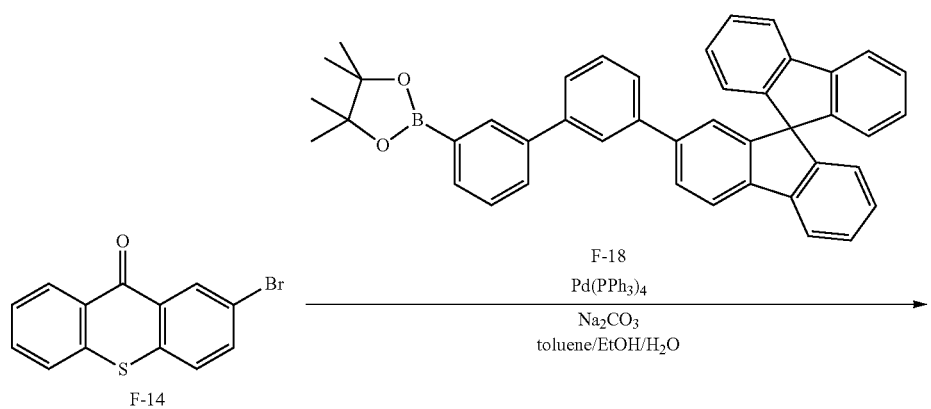

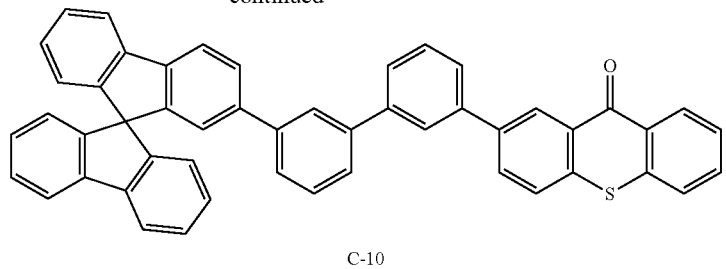

C-10

A 200-mL recovery flask was charged with the following reagents and solvents:
F-14: 1.5 g (5 mmol)
F-18: 3.6 g (6 mmol)
Tetrakis(triphenylphosphine)palladium(0): 137 mg (0.12 mmol)
Toluene: 50 mL
Ethanol: 20 mL
Sodium carbonate aqueous solution (concentration: 30% by weight): 30 mL Then, the atmosphere inside the reaction system was replaced by a nitrogen atmosphere, and thereafter, the reaction solution was stirred under refluxing for 3 hours. After the completion of the reaction, water was added to the reaction solution and further stirred, and a deposited crystal was filtered out. Then, the crystal was washed with water, ethanol and acetone successively to obtain a crude product. Then, the crude product was heated and dissolved in toluene, and hot filtered, and thereafter, recrystallized twice with a toluene solvent to obtain a purified crystal. Then, the obtained crystal was vacuum dried at 100° C., and thereafter, refined by sublimation under the conditions of $1 \times 10^{-4}$ Pa and 320° C. to obtain 2.4 g of high-purity illustrative compound C-10 (yield: 70%).

[MALDI-TOF-MS]

Observed value: m/z=678.87, calculated value: 678.20

Illustrative compound C-10 was measured for the $T_1$ energy by the same method as in Example 1, and the $T_1$ energy was 480 nm in terms of wavelength.

Example 17

In the present Example, an organic light emitting element, in which a positive electrode/a hole transporting layer/a light emitting layer/a hole blocking layer/an electron transporting layer/a negative electrode were provided in order on a substrate, was fabricated by the following method. Here, some of compounds used in the present Example are shown below.

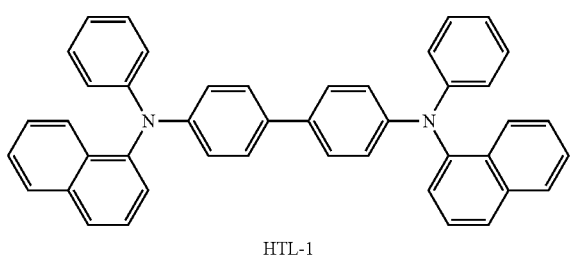

HTL-1

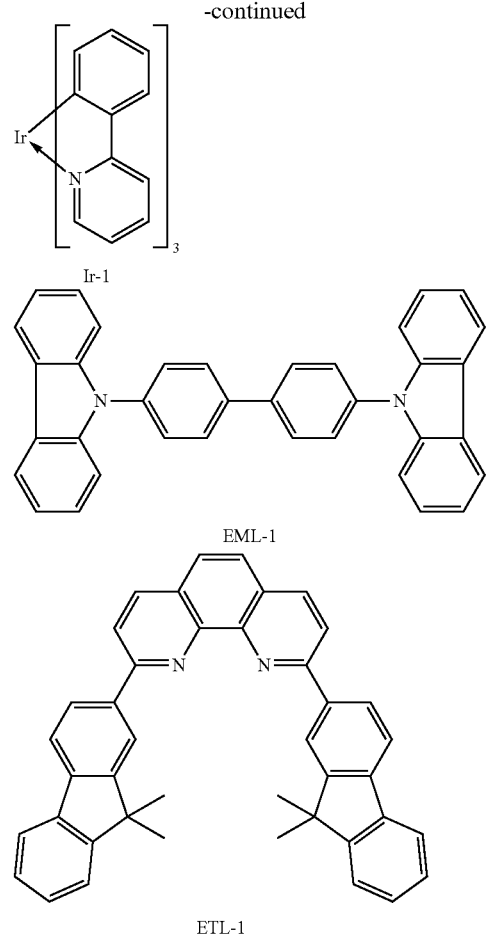

An ITO film was formed on a glass substrate by sputtering to form a positive electrode. At this time, the film thickness of the positive electrode was made 120 nm. The substrate having the ITO electrode formed thereon was used in later steps as a transparent conductive support substrate (ITO substrate). Then, on the ITO substrate, an organic compound layer and an electrode layer indicated in the following Table 4 were formed continuously by vacuum deposition by resistance heating in a vacuum chamber of $1 \times 10^{-5}$ Pa. At this time, the electrode (metallic electrode layer) opposing the ITO electrode was fabricated so that the area of the electrode was made 3 mm².

TABLE 4

| | Constituting Material | Film Thickness [nm] |
|---|---|---|
| Hole Transporting Layer | HTL-1 | 40 |
| Light Emitting Layer | First host: EML-1[note 1] | 30 |
| | Second host: none | |
| | Guest: Ir-1[note 1] | |

TABLE 4-continued

| | Constituting Material | Film Thickness [nm] |
|---|---|---|
| Hole Blocking (HB) Layer | A-3 | 10 |
| Electron Transporting Layer | ETL-1 | 30 |
| First Metallic Electrode Layer (Negative Electrode) | LiF | 0.5 |
| Second Metallic Electrode Layer (Negative Electrode) | Al | 100 |

[note 1]First host:guest = 90:10 (weight ratio)

Then, the organic light emitting element was covered with a protecting glass plate and sealed with an acrylic resin adhesive material in a dry air atmosphere so as not to be degraded due to moisture adsorption. The organic light emitting element was obtained in the foregoing way.

A voltage of 5.1 V was applied to the obtained organic light emitting element with the ITO electrode as its positive electrode and the Al electrode as its negative electrode, and green light emission having a light emission efficiency of 47 cd/A and an intensity of 2,000 cd/m² was observed. The CIE chromaticity coordinate of the element was (x, y)=(0.30, 0.63).

Examples 18 to 29

Elements were fabricated by the same method as in Example 17, except for altering the hole blocking material (HB material) contained in the hole blocking layer (HB layer), and the combination of the first host, the second host and the guest contained in the light emitting layer in Example 17 to those of the following Table 5. The obtained elements were evaluated as in Example 17. The results are shown in Table 5.

TABLE 5

| | Hole Blocking Layer | Light Emitting Layer First Host | Light Emitting Layer Second Host | Light Emitting Layer Guest | Light Emission Efficiency [cd/A] | Voltage [V] | Light Emission Color |
|---|---|---|---|---|---|---|---|
| Example 18 | A-3 | I-3 90 wt % | — | Ir-1 10 wt % | 55 | 5.2 | Green |
| Example 19 | A-3 | I-2 75 wt % | A-3 15 wt % | Ir-7 10 wt % | 48 | 5.4 | Green |
| Example 20 | A-5 | I-3 90 wt % | — | Ir-1 10 wt % | 50 | 5.3 | Green |
| Example 21 | A-9 | I-3 90 wt % | — | Ir-1 10 wt % | 55 | 5.6 | Green |
| Example 22 | A-9 | I-5 75 wt % | A-9 15 wt % | Ir-3 10 wt % | 63 | 5.6 | Green |
| Example 23 | A-17 | I-5 75 wt % | A-17 15 wt % | Ir-16 10 wt % | 10 | 4.8 | Red |
| Example 24 | B-1 | I-5 75 wt % | A-9 15 wt % | Ir-22 10 wt % | 58 | 5.2 | Green |
| Example 25 | B-5 | I-4 90 wt % | — | Ir-13 10 wt % | 35 | 5.8 | Blue green |
| Example 26 | C-2 | I-3 90 wt % | — | Ir-1 10 wt % | 54 | 5.1 | Green |
| Example 27 | I-2 | I-3 75 wt % | C-7 15 wt % | Ir-15 10 wt % | 55 | 6.2 | Green |
| Example 28 | C-10 | I-2 80 wt % | C-10 10 wt % | Ir-7 10 wt % | 56 | 5.5 | Green |
| Example 29 | D-2 | I-6 75 wt % | D-2 15 wt % | Ir-13 10 wt % | 49 | 5.6 | Green |

From Table 5, it is found that the thioxanthone compound according to the present invention could provide a good light emission efficiency by using the compound as an electron transporting material or a light emitting material in an organic light emitting element emitting phosphorescent light.

Examples 30 and 31 and Comparative Example 1

Elements were fabricated by the same method as in Example 17, except for altering the hole blocking material (HB material) contained in the hole blocking layer (HB layer), and the combination of the first host, the second host and the guest contained in the light emitting layer in Example 17 to those of the following Table 6. Here, a compound H-1A used in Comparative Example 1 is shown below.

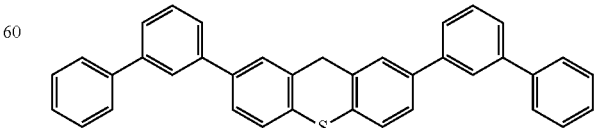

H-1A

The obtained elements were measured for the intensity half-lives of the organic light emitting elements at a current value of 40 mA/cm² in order to evaluate the stability of the elements. The results are shown in Table 6.

TABLE 6

| | Hole Blocking Layer | Light Emitting Layer | | | Intensity Half-life [hr] |
| | | First Host | Second Host | Guest | |
|---|---|---|---|---|---|
| Example 30 | A-3 | I-3 90 wt % | — | Ir-1 10 wt % | 280 |
| Example 31 | A-9 | I-3 90 wt % | — | Ir-1 10 wt % | 310 |
| Comparative Example 1 | H-1A | I-3 90 wt % | — | Ir-1 10 wt % | 90 |

As indicated in Table 6, in the organic light emitting elements emitting phosphorescent light, the thioxanthone compound according to the present invention exhibited longer intensity half-lives than that of the Comparative Example. This is because since the carbonyl skeleton provides a suitable LUMO level, a stable element structure well balanced in charges is made. It is found that this can provide the organic light emitting element with a good element life.

As described above, the thioxanthone compound according to the present invention is a compound having a high $T_1$ energy and a deep LUMO level. Therefore, use of the compound as a constituting material of an organic light emitting element can provide an organic light emitting element which has a high light emission efficiency, is hardly deteriorated, and is stable.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-249278, filed Nov. 8, 2010, which is hereby incorporated by reference herein in its entirety.

The invention claimed is:

1. A thioxanthone compound represented by the following general formula [1]:

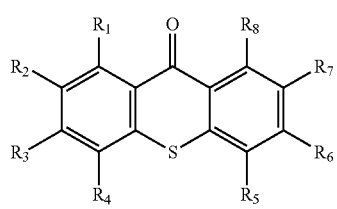

[1]

wherein $R_1$ to $R_8$ are each independently selected from a hydrogen atom or an aryl group selected from the group consisting of a biphenyl group, a naphthyl group, a phenanthrene group, a fluorenyl group, a triphenylenyl group, a dibenzofuranyl group and a dibenzothiophenyl group, provided that at least one of $R_1$ to $R_8$ is the aryl group; and wherein the aryl group may further have an alkyl group, an aromatic hydrocarbon group or an aromatic heterocyclic group.

2. The thioxanthone compound according to claim 1, wherein the $R_1$, $R_4$, $R_5$ and $R_8$ are each a hydrogen atom.

3. An organic light emitting element comprising:
a positive electrode, and a negative electrode; and an organic compound layer disposed between the positive electrode and the negative electrode,
wherein the organic compound layer comprises a thioxanthone compound represented by the following general formula [1]:

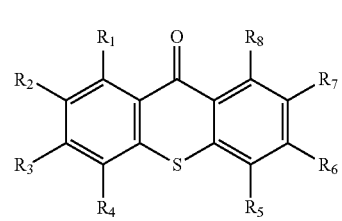

[1]

wherein $R_1$ to $R_8$ are each independently selected from a hydrogen atom, an alkyl group having 1 to 4 carbon atoms, or an aryl group selected from the group consisting of a phenyl group, a biphenyl group, a naphthyl group, a phenanthrene group, a fluorenyl group, a triphenylenyl group, a dibenzofuranyl group and a dibenzothiophenyl group, provided that at least one of $R_1$ to $R_8$ is the aryl group; and wherein the alkyl group and the aryl group may further have an alkyl group, an aromatic hydrocarbon group or an aromatic heterocyclic group.

4. The organic light emitting element according to claim 3, wherein the thioxanthone compound is contained in one of a hole blocking layer and a light emitting layer.

5. The organic light emitting element according to claim 3, wherein:
the thioxanthone compound is contained in the light emitting layer;
the light emitting layer comprises a plurality of hosts and a guest; and
one of the plurality of hosts is the thioxanthone compound.

6. The organic light emitting element according to claim 5, wherein the guest is a phosphorescent light emitting material.

7. The organic light emitting element according to claim 6, wherein the phosphorescent light emitting material is an iridium complex.

8. A display apparatus comprising a plurality of pixels, wherein the pixels each comprise the organic light emitting element according to claim 3, and a switching element connected to the organic light emitting element.

9. An image input apparatus comprising:
a display section to display an image, and an input section to input image information, wherein:
the display section comprises a plurality of pixels; and
the pixels each comprise the organic light emitting element according to claim 3, and a switching element connected to the organic light emitting element.

10. A device comprising a substrate and the organic light emitting device according to claim 3.

11. An illumination apparatus comprising the organic light emitting device according to claim 3.

12. An exposure light source of an image forming apparatus of an electrophotographic system comprising the organic light emitting element according to claim 3.

* * * * *